US011077287B2

(12) United States Patent
Ramanath et al.

(10) Patent No.: US 11,077,287 B2
(45) Date of Patent: Aug. 3, 2021

(54) NON-OCCLUDING BALLOON FOR CARDIOVASCULAR DRUG DELIVERY

(71) Applicant: ANLVR, LLC, Plano, TX (US)

(72) Inventors: Vijay Sitharam Ramanath, Plano, TX (US); Brett Allyn Williams, North Oaks, MN (US)

(73) Assignee: ANLVR, LLC, Plano, TX (US)

( * ) Notice: Subject to any disclaimer, the term of this patent is extended or adjusted under 35 U.S.C. 154(b) by 261 days.

(21) Appl. No.: 16/148,221

(22) Filed: Oct. 1, 2018

(65) Prior Publication Data

US 2019/0099588 A1    Apr. 4, 2019

Related U.S. Application Data

(60) Provisional application No. 62/566,978, filed on Oct. 2, 2017.

(51) Int. Cl.
*A61M 25/10* (2013.01)
*A61M 25/01* (2006.01)

(52) U.S. Cl.
CPC .......... *A61M 25/10* (2013.01); *A61M 25/104* (2013.01); *A61M 25/1029* (2013.01);
(Continued)

(58) Field of Classification Search
CPC .......... A61M 25/10; A61M 2025/1086; A61M 2025/1075; A61M 2025/105;
(Continued)

(56) References Cited

U.S. PATENT DOCUMENTS 4,771,777 A    9/1988  Horzewski et al.
4,790,315 A    12/1988 Mueller et al.
(Continued)

FOREIGN PATENT DOCUMENTS

WO    2014080425 A2    5/2014

OTHER PUBLICATIONS

PCT: International Search Report and Written Opinion of PCT/US18/53859 (related application); dated Dec. 13, 2018; 12 pgs.
(Continued)

*Primary Examiner* — Lauren P Farrar
*Assistant Examiner* — Hamza A Darb

(57) ABSTRACT

A non-occluding drug-coated balloon catheter device for use in a blood vessel transporting blood comprises a catheter shaft including a guidewire lumen, a fluid lumen and a connector port. A balloon is mounted on the catheter shaft and includes an outer envelope surrounding the guidewire lumen in fluid communication with the fluid lumen; a drug coating applied on the exterior surface of the outer envelope; and at least one bypass lumen forming a passage extending from the proximal end of the outer envelope to the distal end of the outer envelope. When the balloon is positioned in a blood vessel and inflated, the exterior surface of the outer envelope presses the drug coating against the blood vessel and the bypass lumen is open between the distal end of the outer envelope and the proximal end of the outer envelope such that blood transport continues through the bypass lumen.

7 Claims, 17 Drawing Sheets

(52) U.S. Cl.
CPC .............. *A61M 2025/0183* (2013.01); *A61M 2025/105* (2013.01); *A61M 2025/1072* (2013.01); *A61M 2025/1075* (2013.01); *A61M 2025/1079* (2013.01); *A61M 2025/1086* (2013.01); *A61M 2025/1097* (2013.01)

(58) Field of Classification Search
CPC ........ A61M 25/104; A61M 2025/1072; A61M 2025/1097; A61M 2025/1079; A61M 2025/0183; A61M 2025/1029
See application file for complete search history.

(56) References Cited

U.S. PATENT DOCUMENTS

| | | | |
|---|---|---|---|
| 5,102,402 A | 4/1992 | Dror et al. | |
| 5,108,370 A | 4/1992 | Walinsky | |
| 5,158,540 A | 10/1992 | Wijay et al. | |
| 5,213,576 A * | 5/1993 | Abiuso | A61M 25/104 604/103.01 |
| 5,269,770 A | 12/1993 | Conway et al. | |
| 5,304,121 A | 4/1994 | Sahatjian | |
| 5,403,280 A | 4/1995 | Wang | |
| 5,433,706 A | 7/1995 | Abiuso | |
| 5,613,948 A | 3/1997 | Avellanet | |
| 6,293,923 B1 | 9/2001 | Yachia et al. | |
| 6,463,317 B1 | 10/2002 | Kucharczyk et al. | |
| 6,506,180 B1 | 1/2003 | Lary | |
| 6,793,664 B2 | 9/2004 | Mazzocchi et al. | |
| 6,847,848 B2 | 1/2005 | Sterzer et al. | |
| 6,986,868 B2 | 1/2006 | Madsen | |
| 7,060,051 B2 | 6/2006 | Palasis | |
| 7,150,853 B2 | 12/2006 | Lee et al. | |
| 7,252,934 B2 | 8/2007 | Boersma et al. | |
| 7,314,480 B2 | 1/2008 | Eidenschink et al. | |
| 7,658,966 B2 | 2/2010 | Kokish | |
| 7,695,674 B2 | 4/2010 | Varma et al. | |
| 7,794,775 B2 | 9/2010 | Stratford et al. | |
| 8,100,961 B2 | 1/2012 | Vyavahare et al. | |
| 8,911,468 B2 | 12/2014 | Ogle et al. | |
| 9,937,255 B2 | 4/2018 | Ogle et al. | |
| 2001/0032004 A1 | 10/2001 | Werneth | |
| 2007/0067010 A1 | 3/2007 | Wang et al. | |
| 2008/0255508 A1 | 10/2008 | Wang | |
| 2009/0069883 A1 | 3/2009 | Ding et al. | |
| 2009/0186370 A1 | 7/2009 | Ogle et al. | |
| 2009/0214654 A1 | 8/2009 | Isenburg et al. | |
| 2009/0270964 A1 | 10/2009 | Huetter et al. | |
| 2010/0016833 A1 | 1/2010 | Ogle et al. | |
| 2010/0119605 A1 | 5/2010 | Isenburg et al. | |
| 2011/0093000 A1 | 4/2011 | Ogle et al. | |
| 2011/0218517 A1 | 9/2011 | Ogle et al. | |
| 2012/0015019 A1 | 1/2012 | Pacetti et al. | |
| 2012/0323211 A1 | 12/2012 | Ogle et al. | |
| 2015/0272732 A1 | 10/2015 | Tilson et al. | |
| 2015/0335866 A1* | 11/2015 | Stapleton | A61M 25/1034 604/103.02 |
| 2017/0071736 A1* | 3/2017 | Zhu | A61M 25/1002 |
| 2017/0252544 A1* | 9/2017 | Gomes | A61M 29/02 |

OTHER PUBLICATIONS

Patent Cooperation Treaty: International Preliminary Report on Patentability of PCT/US2018/053859 (related application); Miki Kobayashi; Apr. 7, 2020; 6 pages.

* cited by examiner

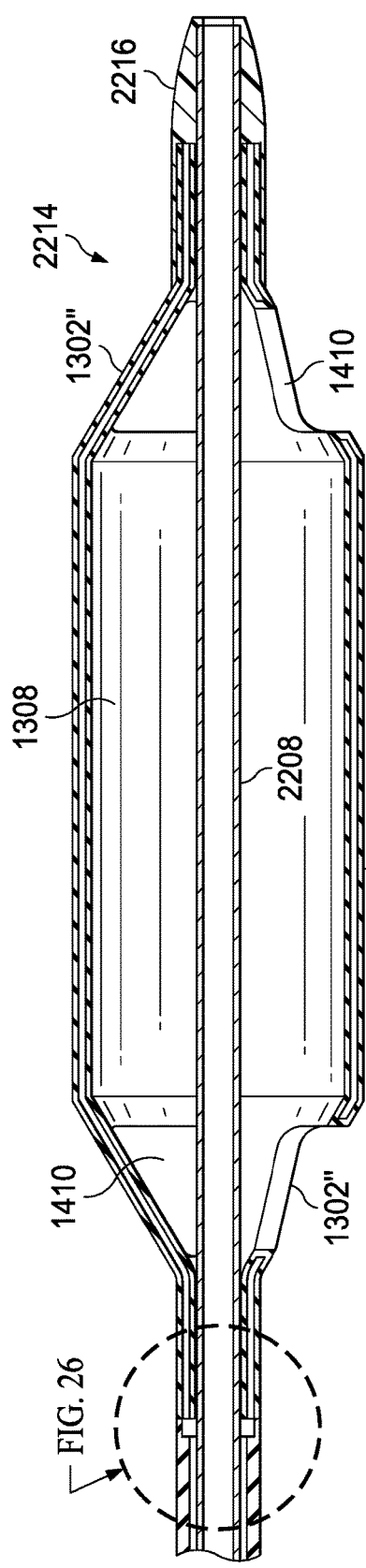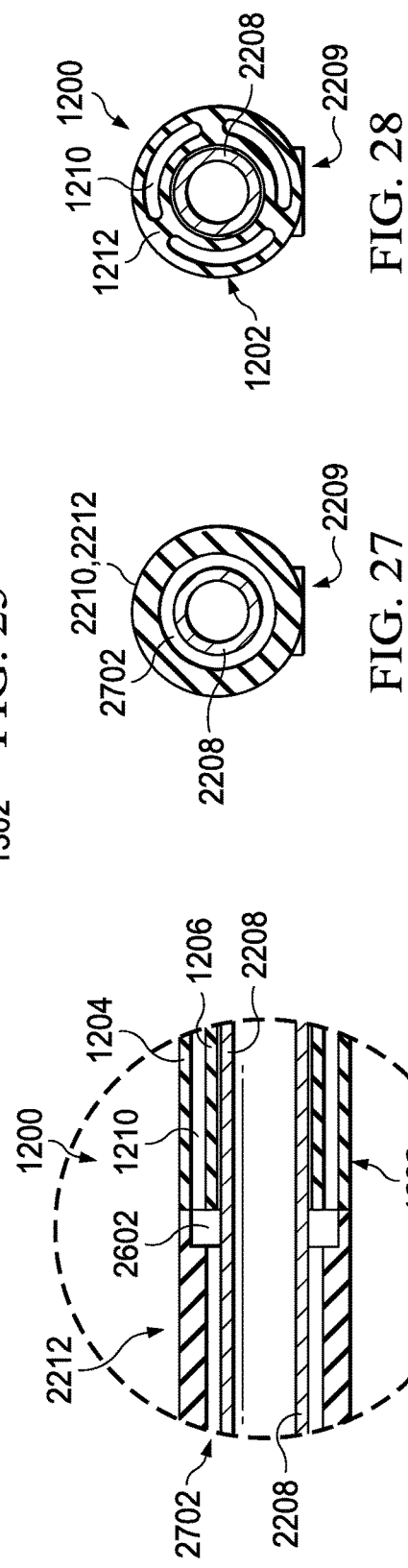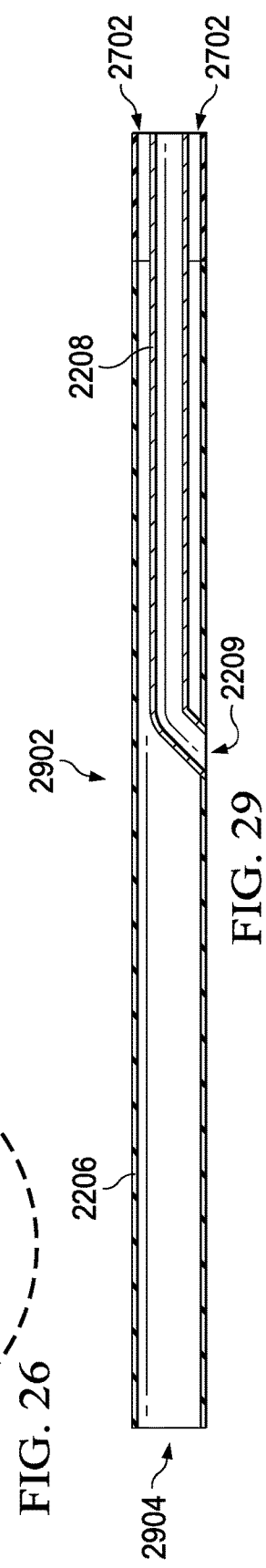

NON-OCCLUDING BALLOON FOR CARDIOVASCULAR DRUG DELIVERY

CROSS-REFERENCE TO RELATED APPLICATIONS

This application claims benefit of U.S. Provisional Application No. 62/566,978, filed, Oct. 2, 2017, the specification of which is hereby incorporated by reference in its entirety.

TECHNICAL FIELD

The following disclosure relates to the field of medical balloons. In particular, it relates to medical balloons for use in the coronary arteries and other vessels of the body, including a drug-coated balloon (DCB) and a drug-releasing balloon that can be used for drug delivery in the coronary arteries and in other vascular beds and structures in the body.

BACKGROUND

Coronary artery disease remains the number one cause of death for both men and women in the developed world. In the United States, an estimated 60,000 Americans die of cardiovascular disease each year; the most common form of cardiovascular disease being coronary artery disease (CAD). About 720,000 people in the United States suffer heart attacks each year. Current percutaneous therapeutic options center around conventional coronary balloon angioplasty and stenting. However these techniques have several limitations. Conventional balloon angioplasty without stent insertion has very limited long-term patency. Current generation coronary drug-eluting stents have improved durability and patency but these devices remain limited by in-stent restenosis and stent thrombosis resulting in recurrent cardiovascular events. Percutaneous treatment options for in-stent restenosis are also limited and include balloon angioplasty and repeat stenting, both of which often have poor long-term patency. Second, stenting often limits future surgical revascularization options. Finally, a subset of coronary artery lesions including small vessel disease, bifurcation lesions and ostial lesions remain a significant challenge for interventional cardiologists due to the complexity of these lesions and unfavorable anatomy. Bifurcation stenting using a two-stent strategy (one stent in the main vessel and an overlapped stent from the main vessel into the side branch) can result in unacceptably high rates of in-stent restenosis with limited future percutaneous options.

Drug-coated balloons (often referred to as "DCBs" or drug-eluting balloons) have been studied in the coronary arteries given the success of drug-coated balloon technology in the peripheral vascular space. Coronary DCBs have primarily been studied in cases of in-stent restenosis, bifurcation lesions, and small vessel lesions. In order for adequate antiproliferative drug elution into the vascular architecture, DCB inflations need to be longer in duration (minimum 30-60 seconds) compared to balloon inflations performed during conventional coronary angioplasty (typically less than 20 seconds). During the extended balloon inflation period, myocardial blood flow ceases and ischemia occurs which can lead to cardiac dysrhythmias, angina, and even hemodynamic instability depending on lesion location and the patient's clinical condition. These issues are concerning to practicing interventionalists, particularly when treating high-risk lesions such as lesions in the proximal coronary arteries (e.g., left anterior descending [LAD] artery and large dominant right coronary artery [RCA]). Thus, the use of drug-coated balloons to treat CAD has been met with significant skepticism.

In order to address the concern of prolonged ischemia during balloon inflation, a need exists for a drug-coated balloon that does not occlude blood flow when inflated for drug elution into the vessel architecture. A need further exists, for both semi-compliant and non-compliant versions of the non-occluding drug-coated balloon in order to appropriately treat a wide array of coronary artery lesions commonly seen in clinical practice.

SUMMARY

A novel drug-coated balloon is provided that is non-occluding when inflated for drug elution. One embodiment of the new drug-coated balloon can be produced in two versions (analogous to conventional coronary balloons), namely: 1) a semi-compliant balloon version believed to be particularly suitable for treatment of de novo lesions; and 2) a noncompliant, balloon version believed to be particularly suitable for treatment of in-stent restenosis. Both versions of this embodiment include a central lumen for the guidewire. Upon inflation, the balloon takes on a "Mercedes-Benz" sign appearance in cross section with three lumens or channels created allowing for passive movement of blood through the balloon during delivery of a drug coated on the balloon. The drug coating can include Paclitaxel, which has been widely studied and used in previous coronary drug-eluting stents and current-generation peripheral arterial DCBs. The blood flow through the lumen(s) of the fully inflated balloon allows for safer and more prolonged balloon inflation times to occur in order to maximize delivery of Paclitaxel or other drugs to the vessel wall and thus increased efficacy of the drug. The balloon can be particularly useful in treating more proximal lesions including proximal bifurcation lesions (e.g. LAD and first diagonal branch).

In one aspect thereof, a non-occluding drug-coated balloon catheter device for use in a blood vessel transporting blood comprises a catheter shaft including a guidewire lumen, a fluid lumen and a connector port. A balloon is mounted on the catheter shaft and includes an outer envelope surrounding the guidewire lumen in fluid communication with the fluid lumen; a drug coating applied on the exterior surface of the outer envelope; and at least one bypass lumen forming a passage extending from the proximal end of the outer envelope to the distal end of the outer envelope. When the balloon is positioned in a blood vessel and inflated, the exterior surface of the drug-coated outer envelope presses the drug coating against the blood vessel wall, while the bypass lumen is open between the distal end of the outer envelope and the proximal end of the outer envelope such that passive blood transport continues through the bypass lumen.

In one embodiment, the balloon is a semi-compliant balloon.

In another embodiment, the balloon is a non-compliant balloon.

In another aspect of the disclosure, a method for fabricating a non-occluding medical balloon for use on a catheter device comprises providing a balloon preform having a sidewall defining a central passage and having at least one inflation passage disposed in the sidewall, blowing the balloon preform into an expanded balloon, filling the balloon with a support medium, sealing, at each end of the balloon, the passage walls together across a portion of the inflation passage and cutting a hole through sealed portion to form a perfusion port, and removing the support medium.

In still another aspect of the disclosure. a method for fabricating a non-occluding medical balloon for use on a catheter device comprises providing a balloon preform having a sidewall defining a central passage and having at least one inflation passage disposed in the sidewall, blowing the balloon preform into an expanded balloon, supporting the inner surface of the expanded balloon, sealing, at each end of the balloon, the passage walls together across a portion of the inflation passage and forming a perfusion port through the sidewall into the central passage, and removing the support from the inner surface of the balloon.

In one embodiment, the method further comprises coating the outer surface of the balloon with a drug-eluting coating.

In another embodiment, the method further comprises boring a plurality of micro-pores through the outer surface of the balloon into the at least one inflation passage.

In yet another embodiment, boring the plurality of micropores is performed before removing the support medium.

In still another embodiment, boring the plurality of micropores is performed after removing the support medium.

In yet another embodiment, supporting the inner surface of the expanded balloon further comprises filling the central cavity of the balloon with conforming support medium and sealing the passage walls together across a portion of the inflation passage and forming a perfusion port through the sidewall further comprises pressing the inflation passage walls together across a portion of the inflation passage against the support medium, sealing a portion of the pressed-together passage walls, and cutting a hole through a portion of the sealed portion.

In a further embodiment, sealing, at each end of the balloon, the passage walls together across a portion of the inflation passage and cutting a hole through sealed portion further comprises sealing the passage walls together and cutting a hole through the sealed portion with a single tool.

In a yet further embodiment, sealing, at each end of the balloon, the passage walls together across a portion of the inflation passage and cutting a hole through sealed portion further comprises sealing the passage walls together with a first tool, and cutting a hole through the sealed portion with a second tool.

In a still further embodiment, the balloon preform includes a plurality of discrete inflation passages disposed between the inner and outer surfaces of the sidewall.

In a still further embodiment, the method further comprises removing at least a portion of the end cone from the blown balloon to expose the inflation passage and inserting a first end of a preformed inflation lumen into the inflation passage of the balloon body. Supporting the inner surface of the expanded balloon further comprises inserting a first mandrel into the central cavity of the balloon and inserting a second mandrel into the preformed inflation lumen. Sealing the passage walls together across a portion of the inflation passage and forming a perfusion port through the sidewall further comprises sealing the first end of the preformed inflation lumen into the inflation passage and sealing the remaining portions of the inflation passage along the edge to one another.

In yet another aspect of the disclosure, a non-occluding medical balloon apparatus comprises a proximal preform portion including a sidewall having an outer surface, an inner surface defining a central passage, and at least one inflation passage disposed between the outer and inner surfaces, a nosecone defining an extension of the central passage, and an expanded balloon portion disposed between, and connected to, the proximal preform portion and the nosecone. The expanded balloon portion includes a substantially cylindrical central portion having a nominal diameter that is greater than a proximal diameter of the proximal preform portion and greater than a distal diameter of the nosecone, a proximal end portion connected between the central portion and the proximal preform portion and tapering from the nominal diameter of the central portion to the proximal diameter of the proximal preform portion, and a distal end portion connected between the central portion and the nosecone and tapering from the nominal diameter of the central portion to the distal diameter of the nosecone. Each of the proximal end portion, central portion and distal end portion include respective expanded sidewalls having respective expanded outer surfaces, respective expanded inner surfaces defining respective expanded central passages, and at least one respective expanded inflation passage disposed between the respective outer and inner expanded surfaces. Each inflation passage of the proximal preform portion is in fluid communication with a corresponding expanded inflation passage of the expanded balloon portion. On each of the proximal and distal end portions of the expanded balloon portion, areas of the outer and inner sidewalls are sealed together, and within each sealed-together area of the outer and inner sidewalls, a hole is cut through the sidewall into the expanded central passage to form perfusion port. A fluid-tight guide wire lumen is disposed through the central passage of the proximal preform portion, the respective expanded central passages of the balloon portion and the central passage of the nose cone.

In one embodiment, the proximal preform portion comprises multiple inflation lumens separated by preform septums, the expanded balloon portion comprises multiple expanded inflation lumens separated by balloon septums, and the respective inflation lumens are in fluid communication with the respective expanded inflation lumens.

In another embodiment, the non-occluding medical balloon apparatus further comprises a drug-eluting coating disposed on the outer surface of the central portion of the balloon.

In yet another embodiment, the drug-eluting coating comprises any drug including, but not limited to, the drug Paclitaxel.

In still another embodiment, the non-occluding medical balloon apparatus further comprises a plurality of micropores formed through the outer surface of the sidewall into the inflation passage.

In a further embodiment, the dimensions of the micropores (denoted by subscript "MP") include a length $L_{MP}$ and a diameter $D_{MP}$, which are selected relative to the surface tension and/or viscosity of a fluid medium within the inflation passage such that the fluid medium is not released from the micro-pores until a predetermined pressure differential $DP_{MP}$ is present between the inflation passage and the exterior of the balloon.

In a yet further embodiment, the non-occluding medical balloon apparatus further comprises a catheter shaft attached to the proximal preform of the balloon, the catheter shaft including a guide wire lumen and an inflation lumen. The guide wire lumen of the catheter shaft is connected to the guidewire lumen of the balloon. The inflation lumens of the catheter shaft are connected to the inflation lumens of the balloon.

BRIEF DESCRIPTION OF THE DRAWINGS

For a more complete understanding, reference is now made to the following description taken in conjunction with the accompanying Drawings in which:

FIG. 25 is a cross-sectional side view of a non-occluding balloon of FIG. 22;

FIG. 26 is a cross-sectional side view of the catheter-to-balloon junction area of the catheter apparatus of FIG. 22;

FIG. 27 is a cross-sectional end view of the proximal preform portion of the balloon taken along line C-C of FIG. 22 showing the rapid exchange guide wire side entry (shaded area);

FIG. 28 is a cross-sectional end view of the catheter shaft taken along line B-B of FIG. 22;

FIG. 29 is a cross-sectional side view of the catheter shaft in the area of the RX guidewire inlet;

FIGS. 39 and 40 shows a non-occluding medical balloon for drug delivery having fabricated perfusion ports and a self-expanding structure in accordance with still another aspect of the disclosure, wherein FIG. 39 shows the self-expanding structure in the collapsed configuration and FIG. 40 shows the self-expanding structure in the expanded configuration.

DETAILED DESCRIPTION

Figure 1:
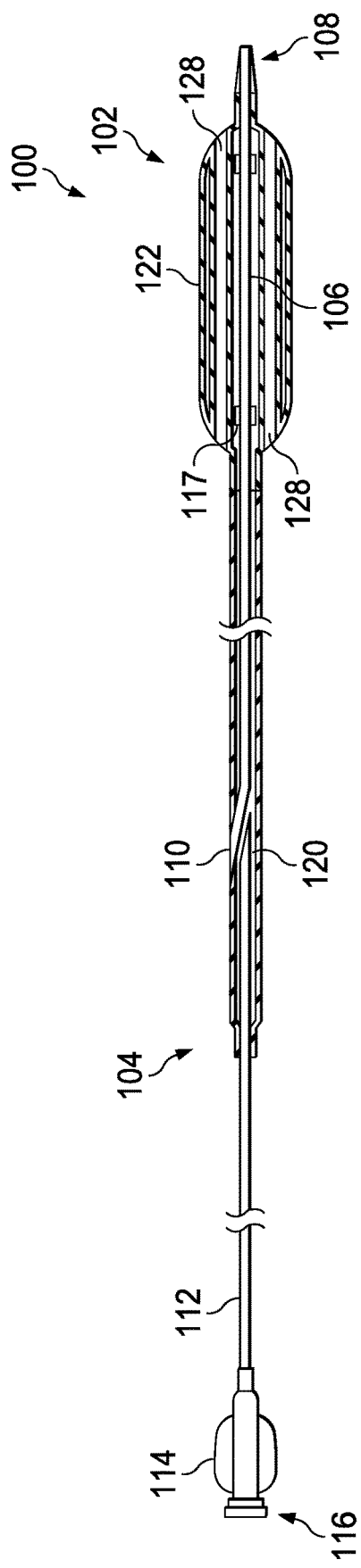
FIG. 1 is a side schematic view of a non-occluding cardiovascular drug-coated balloon and catheter shaft in accordance with one embodiment.

Referring to FIG. 1, there is illustrated a non-occluding cardiovascular drug-coated balloon and catheter shaft device 100 in accordance with one embodiment. The device 100 includes a non-occluding balloon 102 operatively mounted on a catheter shaft 104. In the embodiment shown, the catheter shaft 104 is of the rapid exchange type, having a guidewire lumen 106 extending from a distal end 108 of the shaft to a notch or wire exit 110 located along the shaft. The shaft 104 further includes a proximal hypotube 112 extending from the vicinity of the notch 110 to a fill port connector 114 at a proximal end 116 of the shaft. The balloon 102 is mounted over the distal portion of the guidewire lumen 106 and the distal end of the balloon forms a fluid-tight seal against the guidewire lumen. Radio-opaque markers 117 can be mounted on the guidewire lumen 106 to indicate the proximal and distal ends of the balloon 102 during x-ray imaging. In some embodiment, a tapered tip 118 is attached to the distal end 108 of the shaft. A fluid lumen 120 connects the hypotube 112 to the proximal end of the balloon 102, forming a fluid-tight path from the connector 114 to the interior of the balloon. Saline, contrast solution or other inflation fluid or inflation medium can be introduced into the connector 114 to inflate the balloon 102 via the hypotube 112 and fluid lumen 120. The fluid can be subsequently withdrawn from the connector 114 to deflate the balloon 102. Although a rapid-exchange type catheter shaft 104 is used in the illustrated embodiment of the device 100, other types of catheter shafts (e.g., over-the-wire type) can be used with the non-occluding balloon 102.

The non-occluding balloon 102 includes an outer envelope 122 having a drug coating 124 (see FIG. 2) on an exterior surface 126 and one or more bypass lumens 128 disposed inside the outer envelope having openings on the proximal and distal ends of the outer envelope. For purposes of illustration, the drug coating 124 is shown on only a portion of the exterior surface 126 of the outer envelope 122, but it will be understood that the drug coating covers substantially the entire exterior surface. Prior to balloon inflation, the outer envelope 122 is folded around the catheter shaft so that the majority of the exterior surface 126 is not exposed and the drug coating 124 is protected from being washed away during transit through the body to the treatment site. Upon inflation of the balloon 102, the outer envelope 122 expands and presses the entire exterior surface 126 with the drug coating 124 (now fully exposed) against the adjacent vascular architecture (not shown) so that the drug coating can elute from the balloon onto the tissue for treatment. While the balloon 102 is inflated, the bypass lumens 128 (extending between the proximal and distal ends of the outer envelope 122) are open to allow blood to flow through the balloon (i.e., through the bypass lumens), thereby preventing arterial occlusion.

Figure 2:
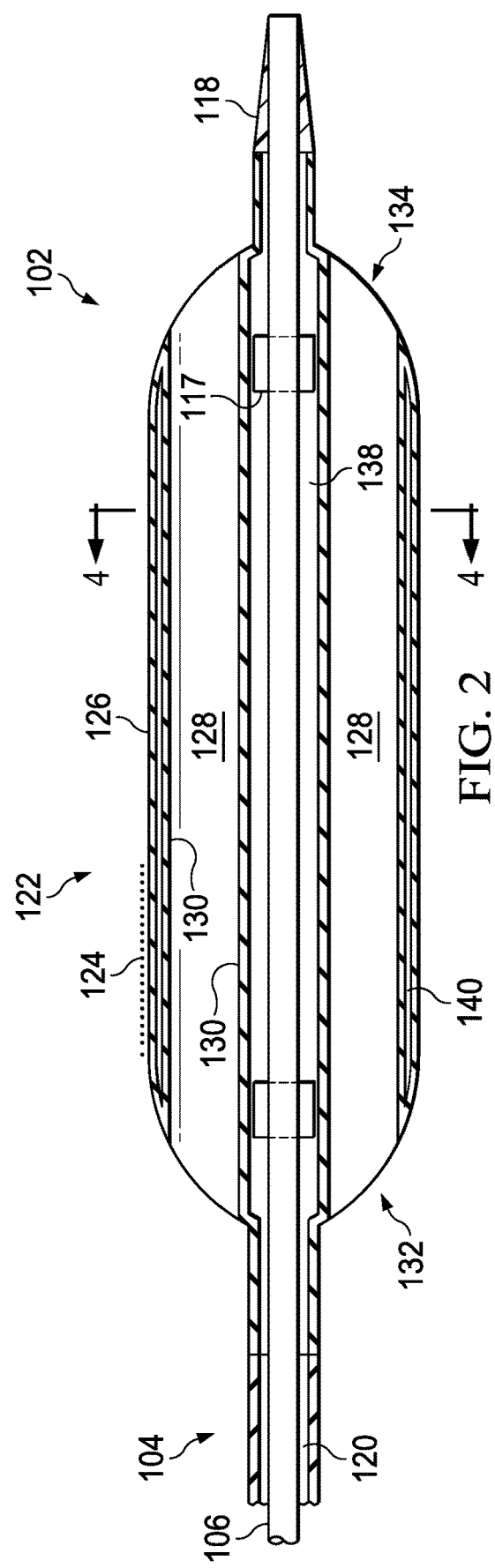
FIG. 2 is a side cross-sectional view of the non-occluding drug-coated balloon of FIG. 1.
Figure 3:
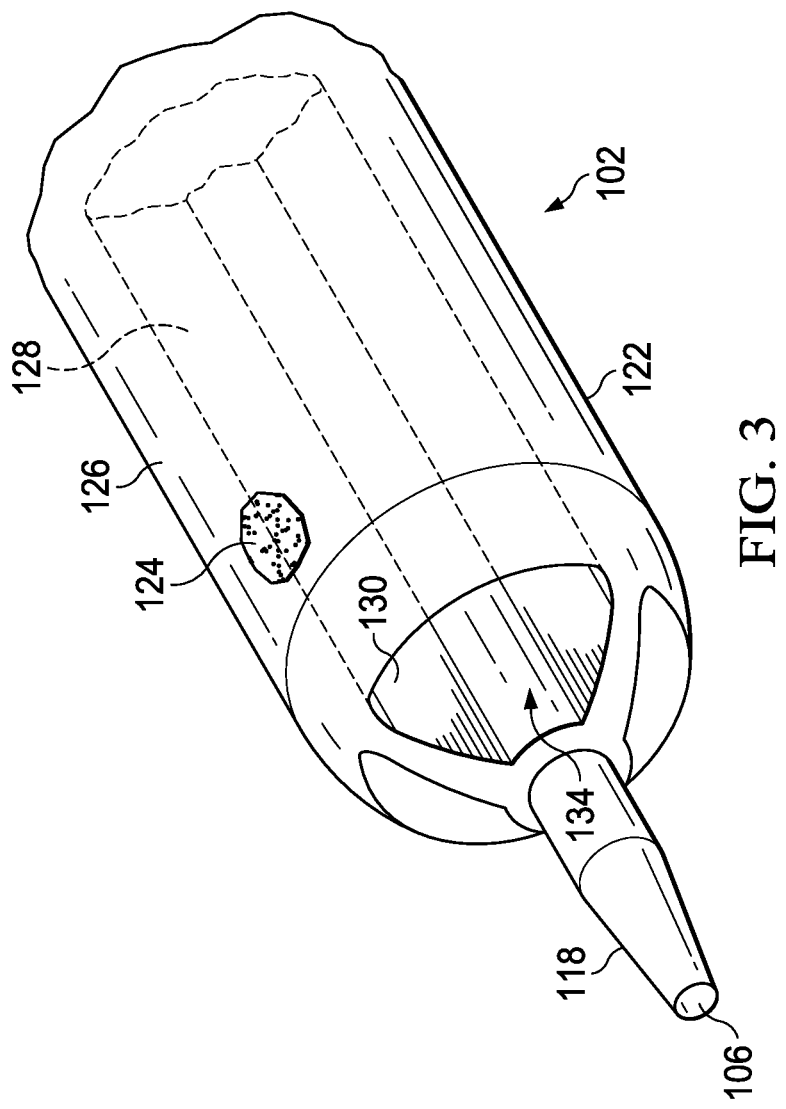
FIG. 3 is a partial front perspective view of the non-occluding drug-coated balloon of FIG. 1.
Figure 4:
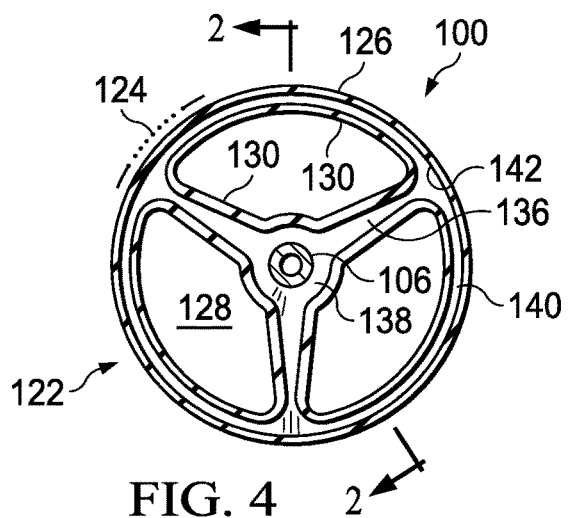
FIG. 4 is a cross-sectional view of the non-occluding drug-coated balloon of FIG. 1.

Referring to FIGS. 2-4, further details of the non-occluding drug-coated balloon 102 are provided. Each bypass lumen 128 is formed by a bypass lumen wall 130 attached to the proximal end of the outer envelope 122 to form a proximal bypass opening 132 and attached to the distal end of the outer envelope to form a distal bypass opening 134. The configuration of the bypass lumens 128 can form spoke passages 136 extending between the central portion 138 of the balloon (near the guidewire lumen 106) and the rim portion 140 (near the outer envelope 122). During inflation of the balloon 102, inflation fluid enters the balloon from the fluid lumen 120, flows from the central portion 138 through the spoke passages 136 and into the rim portion 140 to fully expand the outer envelope 122. In the illustrated embodiment, three wedge-shaped bypass lumens 128 are provided, forming a "three-pointed star" design or "Mercedes-Benz" design when viewed in cross-section. In other embodiments, different numbers of bypass lumens having different cross-sectional shapes can be used.

The non-occluding drug-coated balloon 102 can be constructed of polymer materials including polyether block amide (also known as "PEBA") and polyamides such as nylon. In some embodiments, the ends of the bypass lumens 128 can be joined to the outer envelope 122 using glues or adhesives, by solvent welding or by thermal welding.

Referring now specifically to FIG. 4, in a first embodiment, the wall 142 of the outer envelope 122 can be formed of PEBAX 7033 polyether block amide material having a certain thickness and the walls 130 of the bypass lumens 128 can be formed of PEBAX 7233 polyether block amide material having a greater thickness. The PEBAX 7233 material of the bypass lumen walls 130 is stiffer (i.e., less compliant) than the PEBAX 7033 material of the outer envelope wall 142. This configuration can yield a balloon 102 that is semi-compliant. In one example, a semi-compliant balloon having a nominal diameter of 3.0 mm at a nominal pressure of 6-8 atmospheres can be expected to have a final diameter of 3.3 mm at the burst pressure of 14 atmospheres.

In a second embodiment, the wall 142 of the outer envelope 122 can be formed of PEBAX 7233 polyether block amide material having a thickness of 0.04 mm and the walls 130 of the bypass lumens 128 can also be formed of PEBAX 7233 polyether block amide material having a certain thickness. In this embodiment, the material of the bypass lumen walls 130 is the same as that of the outer envelope wall 142. This configuration can yield a balloon 102 that is non-compliant. In one example, a non-compliant balloon having a nominal diameter of 3.5 mm at a nominal pressure of 12 atmospheres can be expected to have a final diameter of 3.65 mm at the burst pressure of 19-20 atmospheres.

Some embodiments of the non-occluding drug-coated balloon 102 for use in coronary arteries can have a nominal length from 10 mm to 30 mm. In other embodiments, the balloon 102 can have a nominal length from 12 mm to 26 mm. Some embodiments of the non-occluding drug-coated balloon 102 for use in coronary arteries can have a nominal diameter from 2.0 mm to 5.0 mm. In other embodiments, the balloon 102 can have a nominal diameter from 2.5 mm to 4.0 mm.

In addition to the embodiments described above, other embodiments of the non-occluding balloon can have different lengths and/or wall thicknesses and be made of materials including, but not limited to, polyether block amide (e.g., PEBAX® brand by Arkema or Vestamid® E brand by Evonik Industries), polyamides such as nylon, urethane, polyester and polyethylene terephthalate ("PET") and other materials known for use in semi-compliant and non-compliant medical balloons. By selection of the appropriate dimensions and materials, as is known for producing conventional PTCA balloons and other medical balloons, non-occluding balloons in accordance with this disclosure can be produced having desired dimensions, nominal diameters, nominal pressures, final diameters and burst pressures.

Figure 5:
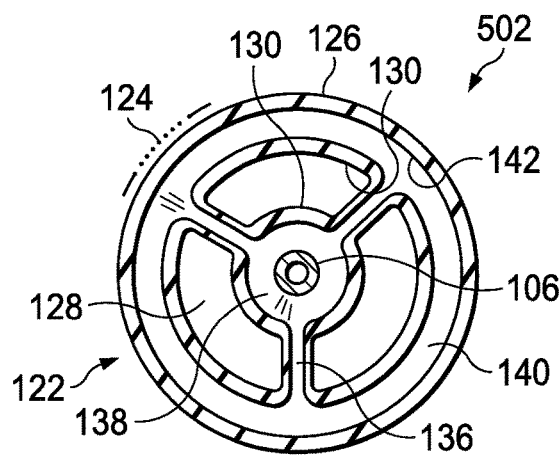
FIG. 5 is a cross-sectional view of a non-occluding drug-coated balloon in accordance with another embodiment.

Referring now to FIG. 5, there is illustrated an alternative non-occluding drug-coated balloon 502. The balloon 502 is substantially similar to the balloon 102 previously described, except the size of the bypass lumens 128 is different from that of the balloon 102. Although the balloon 502 may allow less blood flow through the bypass lumens 128 than the balloon 102, the blood flow is nevertheless sufficient to provide extended drug elution time before significant ischemia occurs. The different sizes of the bypass lumens 128 results in different sized central portion 138, spoke passages 136 and/or outer rim portion 140, which can provide different inflation and stability characteristics for the balloon 502.

Figure 6:
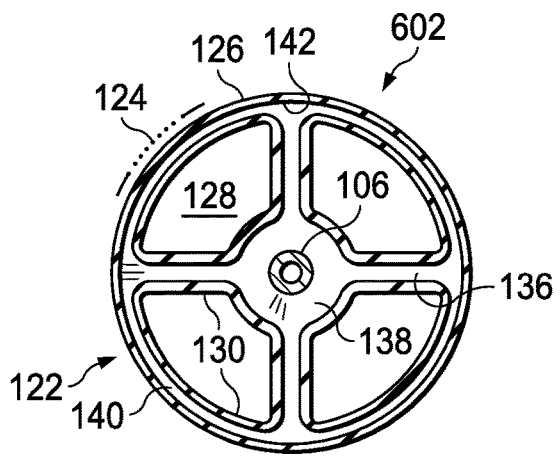
FIG. 6 is a cross-sectional view of a non-occluding drug-coated balloon in accordance with yet another embodiment.

Referring now to FIG. 6, there is illustrated another alternative non-occluding drug-coated balloon 602. The balloon 602 is substantially similar to the balloons 102, 502 previously described, except the number of bypass lumens 128 is different from that of the previous balloons. The different numbers of bypass lumens 128 result in different numbers and shapes of spoke passages 136, which can provide different inflation and stability characteristics for the balloon 602.

Figure 7:
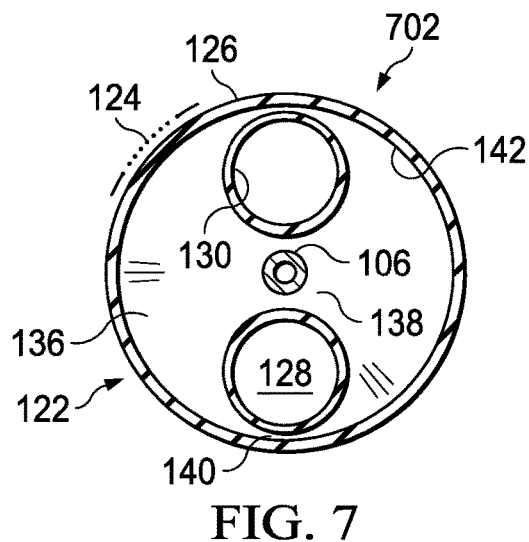
FIG. 7 is a cross-sectional view of a non-occluding drug-coated balloon in accordance with still another embodiment.

Referring now to FIG. 7, there is illustrated another alternative non-occluding drug-coated balloon 702. The balloon 702 is substantially similar to the balloons 102, 502 and 602 previously described, except both the shape and the number of bypass lumens 128 is different from that of the previous balloons. In this embodiment, two bypass lumens 128 are provided, and the lumens have a circular cross section. The different shapes and numbers of bypass lumens 128 result in different numbers and shapes of spoke passages 136, rim portion 140 and central portion 138, which can provide different inflation and stability characteristics for the balloon 702.

Figure 8:
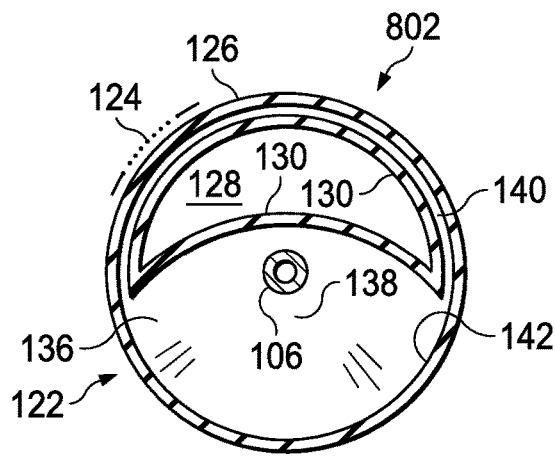
FIG. 8 is a cross-sectional view of a non-occluding drug-coated balloon in accordance with a further embodiment.

Referring now to FIG. 8, there is illustrated a further alternative non-occluding drug-coated balloon 802. The balloon 802 is substantially similar to the balloons 102, 502, 602 and 702 previously described, except both the shape and the number of bypass lumens 128 is different from that of the previous balloons. In this embodiment, only one bypass lumen 128 is provided, and the lumen has a crescent-shaped cross section. The different shapes and numbers of bypass lumen 128 results in different numbers and shapes of spoke passages 136, rim portion 140 and central portion 138, which can provide different inflation and stability characteristics for the balloon 802.

Various processes to fabricate a non-occluding medical balloon are provided in accordance with additional aspects of the invention. In one embodiment, a non-occluding medical balloon with wedge shape windows cut and sealed from the cone region of the balloon consists of the following steps: (1) fabricate the balloon; (2) fill the balloon with a medium having the capability to fill and conform to the interior surface of the balloon and become a ridged substrate to act as a processing aid to allow a tool to press against the surface of the balloon and becoming compressed against the surface of the conforming processing aid; (3) use ultra-sonic energy to cut and seal the balloon (ultra-sonic energy is used because it will have very little radiant heat generated from the process which in turn will not heat effect the balloon); and (4) dissolve the conforming processing aid with a medium that does not exceed 50 degrees Celsius.

Figure 9:
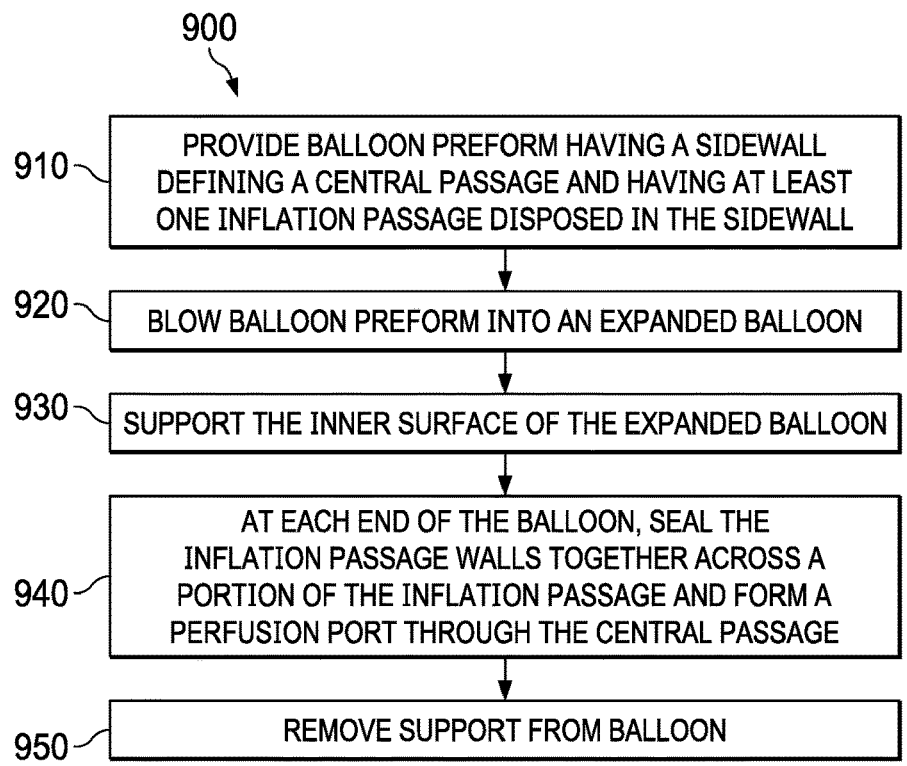
FIG. 9 is a schematic diagram of a method of fabricating a drug-eluting non-occluding medical balloon in accordance with another aspect.

Referring now the FIG. 9, there is illustrated a schematic diagram of a process 900 for fabricating a non-occluding medical balloon for drug delivery in accordance with aspects of the invention. At step 910, a balloon preform is provided having a sidewall defining a central passage and having at least one inflation passage disposed in the sidewall. At step 920, the balloon preform is blown into an expanded balloon. Processes for blow-molding medical balloons are known, and any such process can be used to blow the preform into a balloon (i.e., expanded balloon). Typically, only a center portion of the preform is expanded into the balloon, and the respective end portions of the preform remain relatively unexpanded. The unexpanded portions of the balloon are sometimes referred to as the "tails." In some embodiments, the center portion of the balloon is fully expanded into a cylindrical configuration, and portions proximally and distally adjacent to the center portion are only partially expanded to transition between the tails and the center portion of the balloon. The partially expanded transitional portions of the balloon are sometimes referred to as the "cones" or "end cones." In some embodiments, the step 920 can include heating the balloon preform. If heating is used, in many embodiments the blowing temperature will be limited to 50 degrees C. or less. At step 930, support is provided for the inner surface of the expanded balloon. In some embodiments the support can be provided by a removable conforming medium and in other embodiments the support can be provided by a removable structure such as a mandrel. At step 940, at each end of the balloon, the inflation passage walls are sealed together across a portion of the inflation passage and a perfusion port (i.e., bypass lumen) is formed through the central passage of the balloon. At step 950, the support is removed from the inner surface of the balloon. In some embodiments, the step 950 can include heating a conforming support medium and/or dissolving the support medium with an appropriate solvent. In other embodiments, the step 950 can include removing mandrels from the balloon. Additions steps can be included in process 900 to further adapt the non-occluding balloon for drug delivery. For example, in some embodiments, a drug-eluting coating can be applied to the outer surface of the non-occluding balloon. In other embodiments, micro-pores can be formed through the outer surface of the sidewall of the non-occluding balloon into the inflation passage to allow drug delivery by emission of drug-carrying inflation medium through the micro-pores as disclosed herein.

Figure 10:
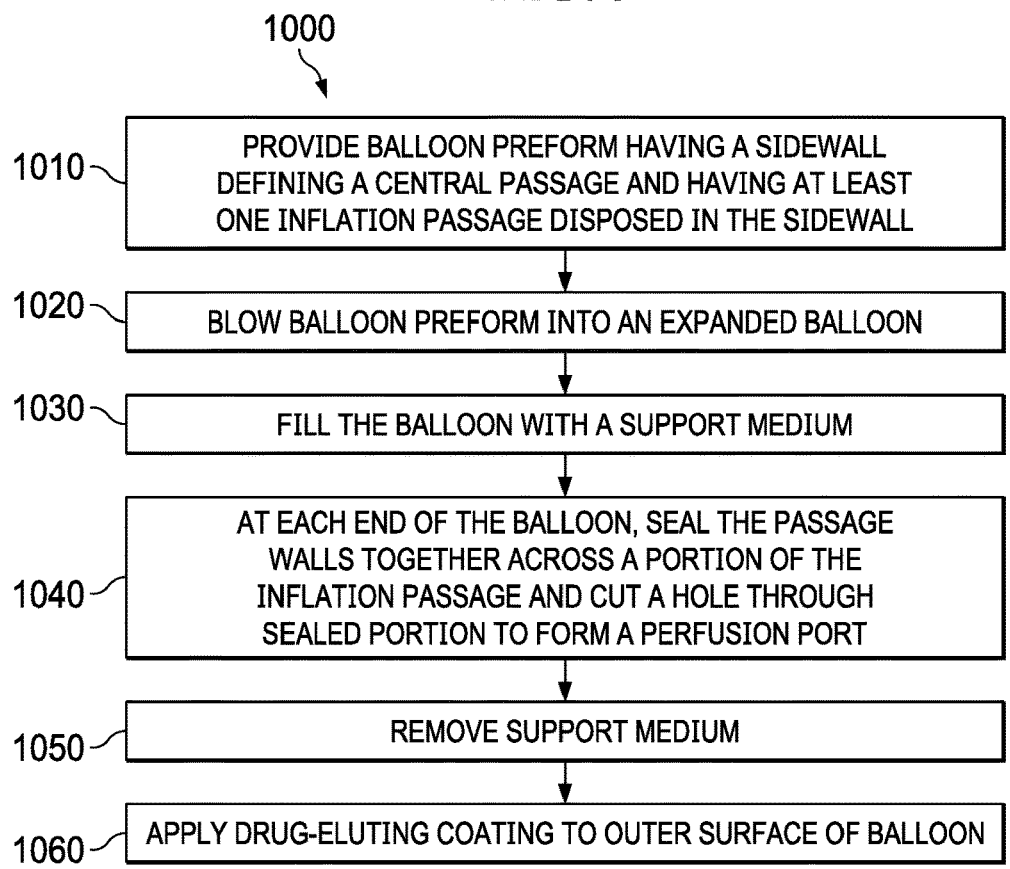
FIG. 10 is a schematic diagram of a method of fabricating a non-occluding medical balloon in accordance with yet another aspect.

Referring now the FIG. 10, there is illustrated a schematic diagram of another process 1000 for fabricating a non-occluding medical balloon for drug delivery in accordance with aspects of the invention. At step 1010, a balloon preform is provided having a sidewall defining a central passage and having at least one inflation passage disposed in the sidewall. At step 1020, the balloon preform is blown into an expanded balloon. As disclosed above, processes for blow-molding medical balloons are known, and any such process can be used to blow the preform into a balloon. In some embodiments, the step 1020 can include heating the balloon preform. If heating is used, in many embodiments the blowing temperature will be limited to 50 degrees C. or less. At step 1030, the balloon is filed with a support medium. The support medium can be any medium that can conform to the inner surface of the balloon and be removed. Various removable media known for use in fabricating medical balloons can be used for the support medium including, but not limited to, solid materials having a melting temperature below the reflow temperature of the balloon material, solid materials soluble in solvents that do not attack the balloon material, and granular or particulate materials. At step 1040, at each end of the balloon, seal the passage walls together across a portion of the inflation passage and cut a hole through sealed portion to form a perfusion port (i.e., bypass lumen). At step 1050, the support medium is removed. In some embodiments, the step 1050 can include heating the support medium and/or dissolving the support medium with an appropriate solvent. At step 1060, a drug-eluting coating is applied to the outer surface of the balloon. In other embodiments, in addition to, or instead of applying a drug-eluting coating to the outer surface of the balloon, micro-pores can be formed through the outer surface of the sidewall into the inflation passage to allow drug delivery by emission of drug-carrying inflation medium through the micro-pores as disclosed herein.

Figure 11:
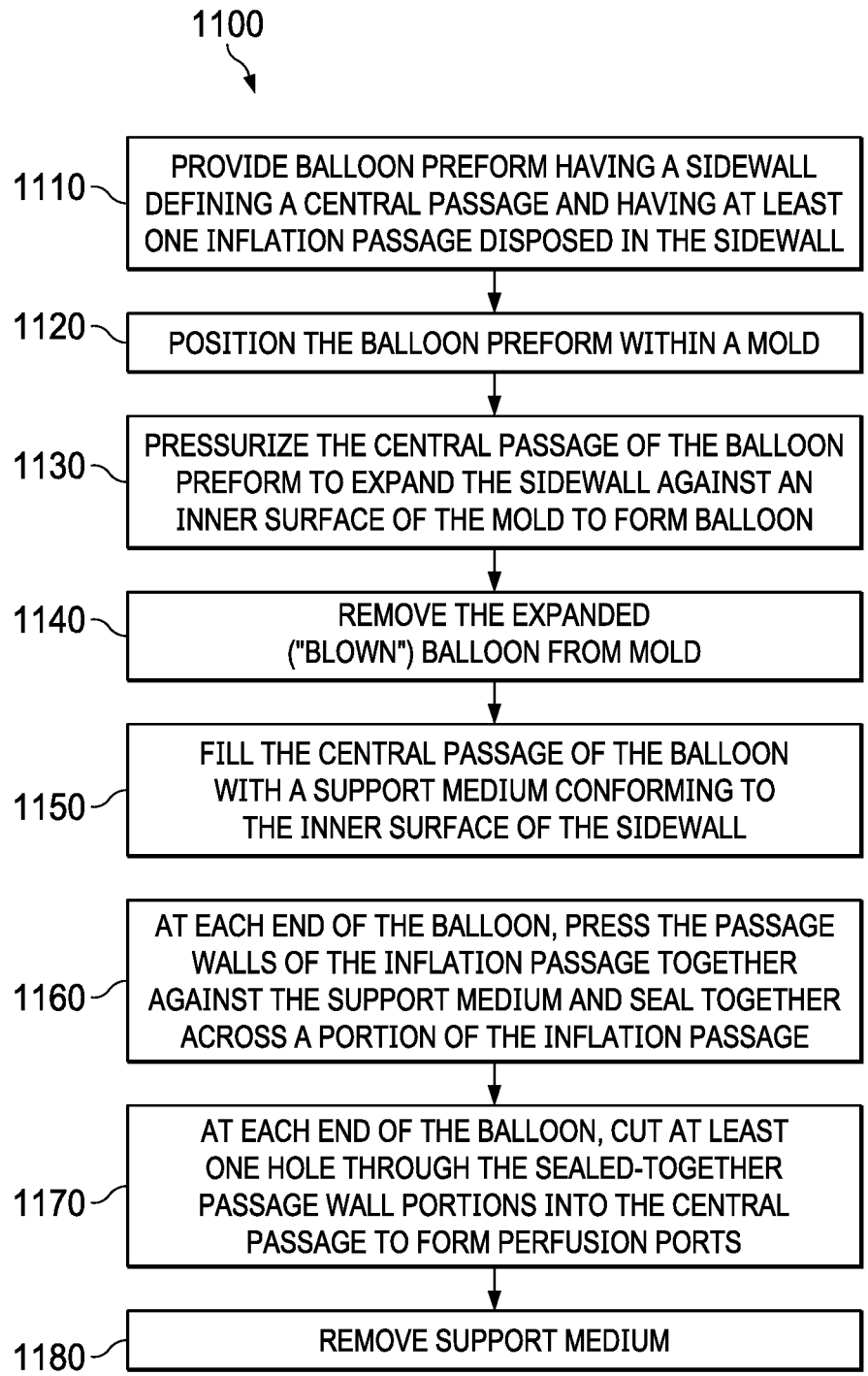
FIG. 11 is a schematic diagram of another method of fabricating a non-occluding medical balloon in accordance with a further embodiment.

Referring now to FIG. 11, there is illustrated a schematic diagram of yet another process 1100 for fabricating a non-occluding medical balloon in accordance with aspects of the invention. At step 1110, a balloon preform is provided having a sidewall defining a central passage and having at least one inflation passage disposed in the sidewall. At step 1120, the balloon preform is positioned within a mold. At step 1130, the central passage of the balloon preform is pressurized to expand the sidewall against an inner surface of the mold to form the balloon. Typically, only a center portion of the preform is expanded when blowing the balloon, e.g., the central portion (i.e., the "cylinder") and adjacent transitional portions (i.e., the "cones"), and the respective end portions of the original preform remain relatively unexpanded in the balloon (i.e., forming the "tails"). In some embodiments, the step 1130 can include heating the balloon preform and/or heating the mold. If heating is used, in many embodiments the temperature of the mold and/or preform will be limited to 50 degrees C. or less. At step 1140, the expanded (i.e., "blown") balloon is removed from the mold. At step 1150, the central passage of the balloon is filled with a support medium conforming to the inner surface of the sidewall. The support medium can be any medium that can conform to the inner surface of the balloon and be removed. Various removable media known for use in fabricating medical balloons can be used for the support medium including, but not limited to, solid materials having a melting temperature below the reflow temperature of the balloon material, solid materials soluble in solvents that do not attack the balloon material, and granular or particulate materials. At step 1160, at each end of the balloon, the passage walls of the inflation passage are pressed together against the support medium and sealed together across a portion of the inflation passage. In some embodiments, the inflation passage walls pressed together and sealed are disposed on the cone ends of the balloon. At step 1170, at each end of the balloon, at least one hole is cut through the sealed-together passage wall portions into the central passage to form perfusion ports. At step 1180, the support medium is removed. In some embodiments, the step 1180 can include heating the support medium and/or dissolving the support medium with an appropriate solvent.

Figure 12:
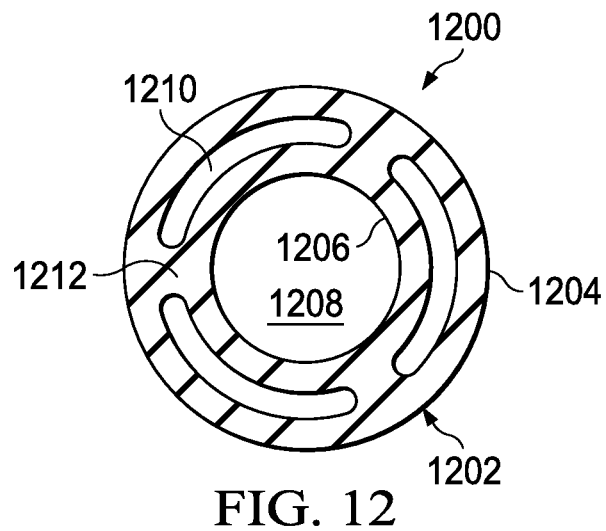
FIGS. 12 and 13 are, respectively, cross-sectional views of a balloon preform and an expanded balloon in accordance with a still further aspect.

Referring still to FIG. 11, in some embodiments, the step 1110 can also comprise: a balloon preform is provided having a sidewall defining a central passage and having a plurality of discrete inflation passages disposed between the inner and outer surfaces of the sidewall. In some embodiments, the step 1120 can also comprise: the balloon preform is positioned within a mold having an inner surface defining a central portion between two end (e.g., cone) portions. In some embodiments, the step 1130 can also comprise: the central passage of balloon preform is pressurized to expand balloon sidewall against the mold inner surface to form balloon having central portion between two end portions (e.g., end cone portions). Typically, only a central portion of the preform is expanded into the balloon, and the two end portions remain relatively unexpanded Referring now to FIG. 12, there is illustrated a cross-sectional end view of an exemplary balloon preform 1200 that can be used in the fabricating a non-occluding medical balloon in accordance the disclosure. The preform 1200 includes a sidewall 1202 having an outer surface 1204 and an inner surface 1206 defining a central passage 1208. Disposed in the sidewall 1202 between the inner surface 1206 and outer surface 1204 is at least one inflation passage 1210. The respective outer and inner surfaces 1204, 1206 of the sidewall 1202 effectively constitute an outer sidewall and an inner sidewall where separated by the inflation passage 1210. The central passage 1208 and inflation passages 1210 can extend continuously through the balloon preform 1200. In the embodiment shown, the preform 1200 includes three inflation passages 1210; however, other embodiments may have different numbers of inflation passages. In the embodiment shown, the each inflation passages 1210 has a "sausage shaped" cross section; however, other embodiments may have inflation passages of different cross-sectional shapes, When the preform 1200 includes multiple inflation passages 1210, the sidewall 1202 can include septums 1212 of continuous material extending from the inner surface 1206 to the outer surface 1204 between adjacent inflation passages.

The balloon preform 1200 can be formed from materials including, but not limited to, PEBAX® brand polyether block amide, nylon and other polyamides, urethane, polyester, polyethylene terephthalate (PET) and other materials known for use in semi-compliant and non-compliant medical balloons. The balloon preform 1200 is preferably formed by extrusion; however, other fabrication methods can be used including, but not limited to, machining, molding and casting.

Figure 13:
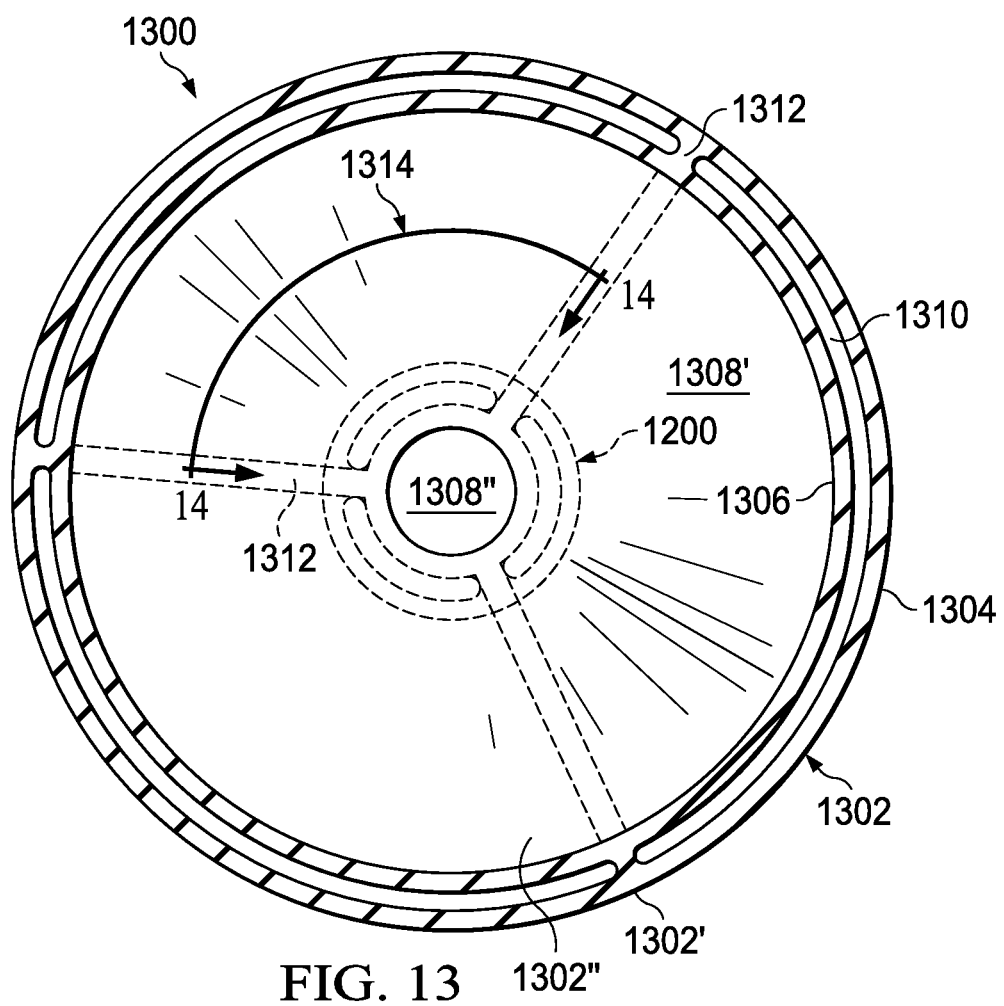

Referring now to FIG. 13, there is illustrated a cross-sectional end view of an exemplary expanded balloon 1300 that can be formed from the balloon preform 1200 and used in fabricating a non-occluding medical balloon in accordance the disclosure. As described above, the balloon preform 1200 is blown into the balloon 1300 according to known blow-molding processes. During the blow-molding process, the sidewall 1202 of the preform 1200 can reform (e.g., by stretching and/or expanding) into a sidewall 1302 of the balloon 1300, and the original preform structures including outer surface 1204, inner surface 1206, central passage 1208, inflation passages 1210 and septums 1212 can reform into corresponding balloon structures including outer surface 1304, inner surface 1306, central passage 1308, inflation passages 1310 and septums 1312. Similar to the preform 1200, the respective outer and inner surfaces 1304, 1306 of the balloon sidewall 1302 effectively constitute a balloon outer sidewall and a balloon inner sidewall where separated by the inflation passage 1310. The fully-expanded portion of the sidewall 1302 (i.e., disposed in the central portion of the balloon) is denoted 1302' in FIG. 13, whereas the partially-expanded portion of the sidewall (e.g., disposed on the end portions of the balloon and extending from the unexpanded portion of the preform 1200 to the fully-expanded portion 1302') is denoted 1302". In FIG. 13, an unexpanded end portion of the balloon preform 1200 (shown in dashed line) can be seen behind the expanded balloon sidewall 1302". The central passage 1308 of the balloon is relatively large (denoted 1308') in the central portion of the balloon and relatively small (denoted 1308") near the preform 1200, expanding therebetween in the end portions of the balloon. View line 14-14 (denoted by arrow 1314) denotes a region on the end portion of the balloon sidewall 1302" where the simplified cross-sections are taken for FIGS. 14A-14E described below.

Referring now to FIGS. 14A-14F, a series of simplified cross-sectional views through the end portion sidewall 1302" of the balloon 1300 are provided to further illustrate the process of forming a non-occluding medical balloon in according with this disclosure. For purposes of simplified illustration, the end portion sidewalls in FIGS. 14A-14F are depicted as straight, although in actuality the sidewalls can be curved as shown in FIG. 13.

Figure 14A:
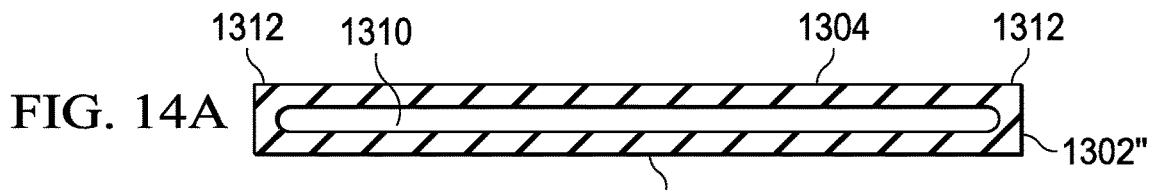
FIGS. 14A-14F are schematic diagrams further illustrating method of fabricating non-occluding medical balloons.

Referring first to FIG. 14A, a portion of the end sidewall 1302" is shown extending between two septums 1312. The inflation passage 1310 is disposed between the outer and inner surfaces 1304, 1306 of the sidewall 1302" (i.e., the balloon outer and inner sidewalls). In the illustration, the inflation passage 1310 is illustrated with the outer sidewall surface 1304 spaced-apart from inner sidewall surface 1306; however, in some embodiments the inflation passage may be collapsed such that the outer and inner sidewall surfaces 1304, 1306 are touching one another (but not bonded together).

Figure 14B:
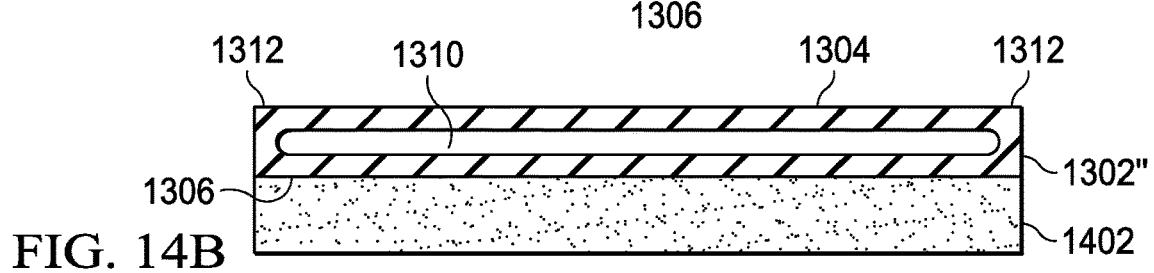

Referring next to FIG. 14B, the inner portion of the balloon (i.e., the central channel 1308) is filled with a support medium 1402 that conforms to the inner surface 1306 of the sidewall 1302". The support medium 1402 provides support for the inner surface 1306 of the sidewall.

Figure 14C:
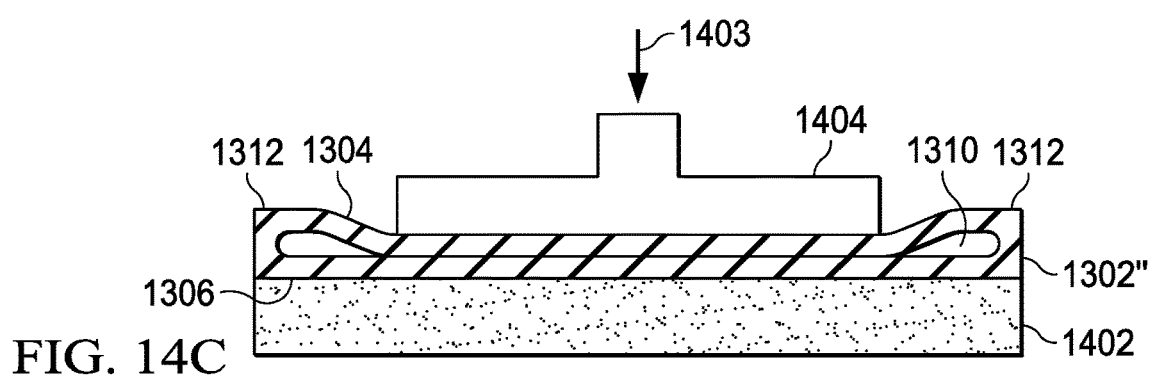

Referring next to FIG. 14C, an area of the outer surface (i.e., outer sidewall) 1304 of the sidewall 1302" is pressed by an external force (denoted by arrow 1403) across the inflation passage 1310 towards an underlying area of the inner surface (i.e., inner sidewall) 1306. Since the inner surface 1306 is supported by the support medium 1402 and cannot move away, the external force 1403 can press areas of the outer surface 1304 into contact with areas of the inner surface 1306. In the embodiment shown in FIG. 14C, a tool 1404 is used to apply the external force 1403 pressing the outer surface 1304 against the inner surface 1306; however, in other embodiments the pressing can be provided by other means including, but not limited to, the application of pressurized fluids including air, inert gas and/or water.

Figure 14D:
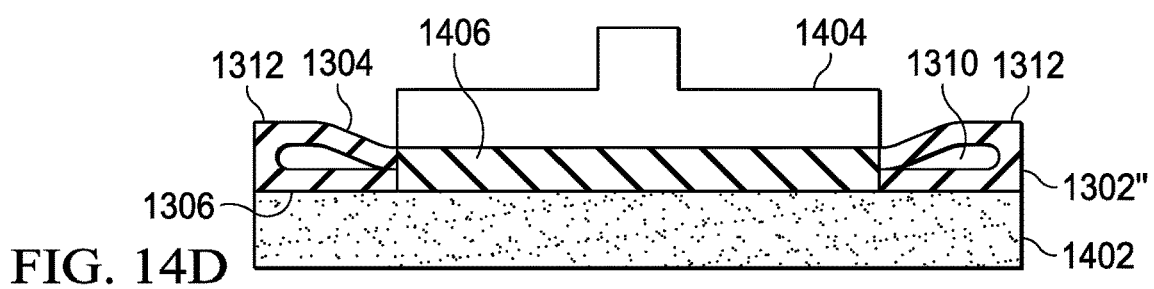

Referring next to FIG. 14D, while an area of the outer surface 1304 is pressed into contact with an area of the inner surface 1306, at least a portion of the pressed-together areas are sealed or fused to one another to produce a sealed portion, denoted 1406. The sealing or fusing can be performed by heating, melting, welding or otherwise joining the respective areas of surfaces 1304 and 1306 to one another to form a pressure-tight bond in the sealed area 1406. Preferably, any application of heat to the area of the sealed portion 1406 is rapid and localized to minimize effects to the surrounding areas of the balloon sidewall 1302". In some embodiments, the tool 1404 both presses the sidewall surfaces 1304 and 1306 together and creates the seal. For example, in various embodiments the tool 1404 can be a heated tool, a sonic (including ultrasonic) welding tool, a radio frequency (RF) welding tool or other known tools for joining balloon materials. In other embodiments, one mechanism (e.g., a tool or compressed fluid) can be used to press the sidewall surfaces 1304 and 1306 together while a second tool (not shown) produces the seal. For example, the second tool can be a heat tool, a sonic/ultrasonic welding tool, a RF welding tool, a microwave welding tool or a laser welding tool. A portion of the inflation passage 1310 remains open after the sealed portion 1406 is created. In the embodiment illustrated in FIG. 14D, the inflation passage 1310 remains open on both sides of the sealed portion 1406; however, in other embodiments, the inflation passage can remain open on only one side of the sealed portion. In yet other embodiments, multiple sealed portion 1406 can be created in the inflation passage 1310 between two septums 1312, and multiple portions of the inflation passage can remain open between such sealed portions.

Figure 14E:
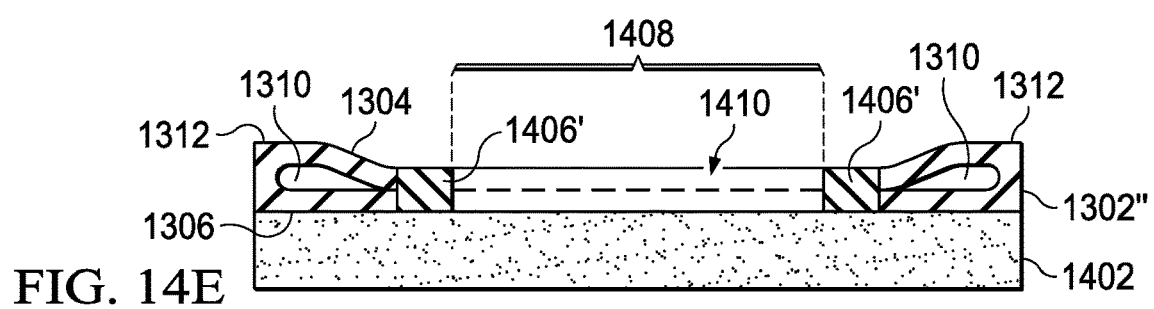

Referring next to FIG. 14E, after creating the sealed portion 1406, an area (denoted 1408) within the sealed portion can be cut away, creating a hole 1410 entirely through the sidewall 1302" into the central passage 1308 of the balloon 1300. This hole 1410 will be the perfusion port (i.e., bypass lumen) of the non-occluding balloon. The remaining (i.e., uncut) portions of the sealed portion (denoted 1406') completely surround the hole 1410 such that the edges of the outer and inner surfaces 1304 and 1306 remain sealed together and the remaining inflation passages 1310 remain fluid-tight. The cutting of the area 1408 of the sealed portion 1406 can be performed using known mechanical cutting mechanisms including knives, cutting blades or punches, or using known thermal cutting mechanisms including heated tools, or using known laser cutting or laser ablation mechanisms. In some embodiments, the same tool 1404 can be used to perform pressing, sealing and cutting operations. In other embodiments, different tools can be used for the various pressing, sealing and cutting operations. In some embodiments, the pressing, sealing and cutting operations can be performed simultaneously, whereas in other embodiments, the various pressing, sealing and cutting operations can be performed sequentially.

Figure 14F:
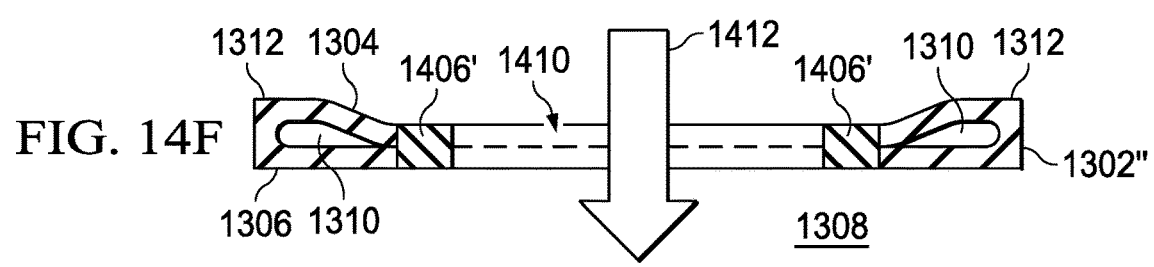

Referring next to FIG. 14F, after creating the hole 1410 through the balloon sidewall 1302", the support medium 1402 can be removed from the central passage 1308 of the balloon 1300. The hole 1410 now forms a perfusion port allowing for the ready passage of fluids such as blood (denoted by arrow 1412) from the exterior of the balloon (e.g., from a blood vessel or other body lumen) through the end sidewall 1302" and into the expanded central passage 1308'. Similar perfusion ports on the opposite end of the balloon 1300 allow fluids 1412 to exit the expanded central passage 1308' and return to the exterior of the balloon (e.g., back into the blood vessel or body lumen).

Figure 15:
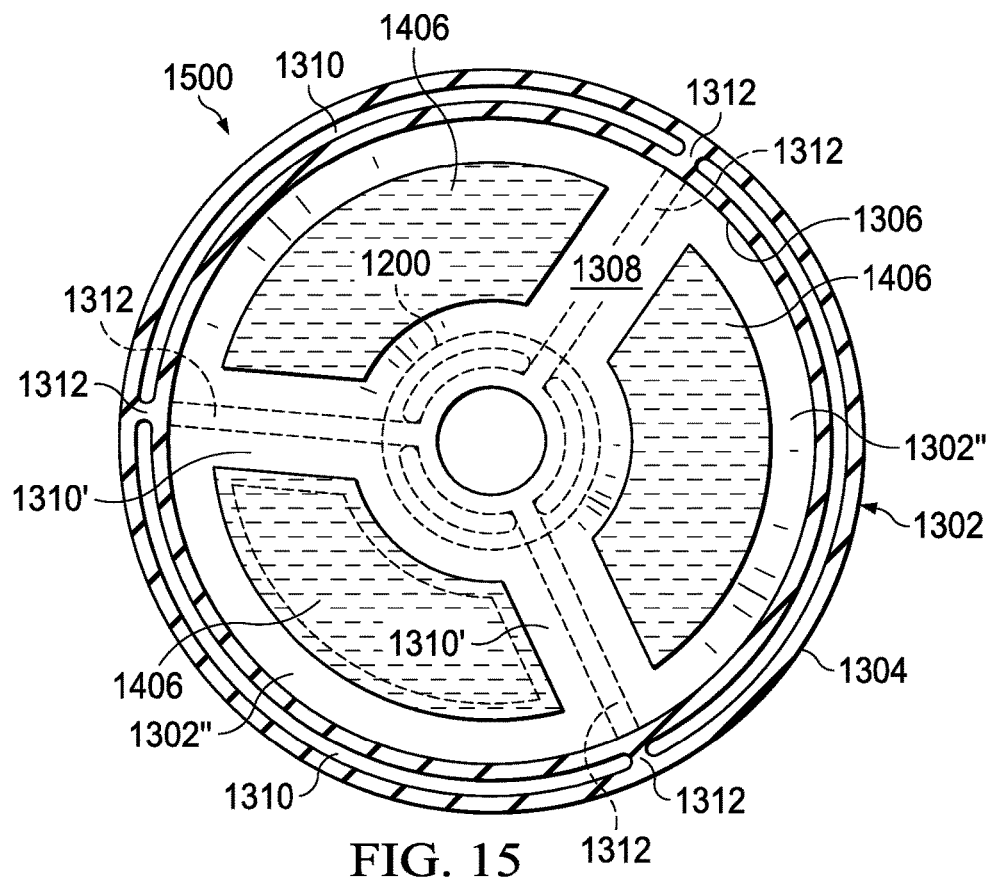
FIGS. 15 and 16 are cross-sectional end views of an expanded balloon further illustrating aspects of the disclosure.

Referring now to FIG. 15, the fabrication of an exemplary non-occluding medical balloon 1500 in accordance with the disclosure is further illustrated and described. The balloon 1500 is substantially similar in many respects to the balloon 1300 previously described, therefore common reference numbers are used for similar elements. In the embodiment of FIG. 15, the end sidewall 1302" includes three inflation passages 1310 separated by three septums 1312. The inflation passages 1310 and septums 1312 can be seen at the exposed cross-sectioned surface and extending down (shown in dashed lines) the end portion of the balloon 1500 to the unexpanded preform 1200. During fabrication of the balloon 1500, the central cavity 1308 can be filled with support medium 1402 conforming to the inner surface 1306; however, the support medium is not shown in FIG. 15 for clarity of illustration.

Referring still to FIG. 15, three sealed portions 1406 can be formed in the sidewall 1302 by pressing the outer and inner surfaces 1304 and 1306 together across areas of the inflation passages 1310 and sealing or fusing areas of the pressed-together surfaces to form a fluid-tight seal, for example as described in connection with FIGS. 14A-14F. Some portions (denoted 1310') of the inflation passage 1310 are left unsealed between the sealed portion 1406 and the septums 1312 so that an inflation medium can travel through the sidewall 1302 of the balloon around the sealed portions. An inner portion of each sealed area 1406 can be selected to be cut out, as denoted by dashed line 1502 in one portion.

Figure 16:
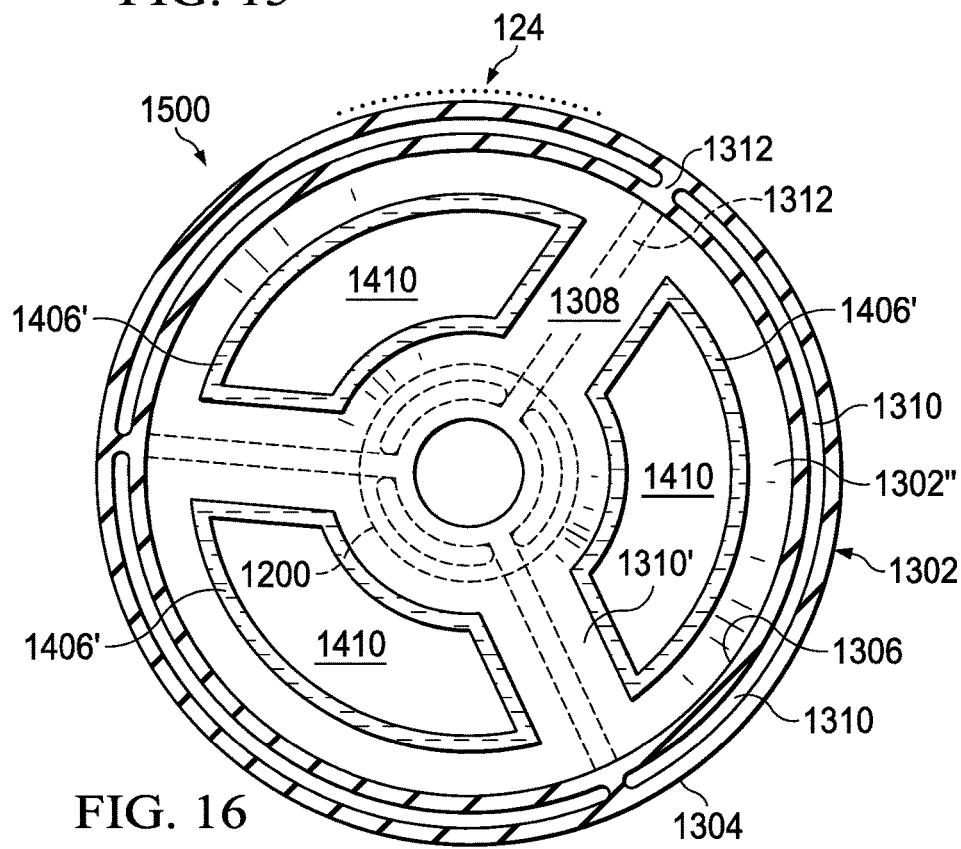

Referring now to FIG. 16, the balloon 1500 is illustrated after the holes 1410 are cut through the sealed portions 1406 to create the perfusion ports, and after the support medium 1402 is removed from the central passage 1308. As previously described, unsealed portions 1310' of the inflation passages remain between the sealed portions 1406' bordering the holes 1410 and the septums 1312 so that an inflation medium can travel from the unexpanded preform end portion 1200, up the proximal end portion sidewall 1302", through the central sidewall 1302' and into the distal end portion sidewall 1302", thereby inflating the balloon 1500. When the balloon 1500 is fully expanded, the perfusion ports 1410 through each end sidewall 1302 allow fluids such as blood to flow through the central passage 1308 of the balloon, thus allowing the balloon to be inflated against blood vessel/body lumen walls without occluding the flow of blood through the vessel or body lumen. In some embodiments, a drug-eluting coating 124 can be applied to the outer surface 1304 of the balloon 1500 to provide a non-occluding medical balloon for drug delivery, in particular for targeted drug delivery to the walls of a blood vessel or body lumen.

As disclosed herein, a non-occluding medical balloon in accordance with aspects of this disclosure can be used for drug delivery using a drug-eluting coating 124 applied to some or all of the outer surface 126 (e.g., FIG. 2) or the outer surface 1304 of the sidewall 1302 (e.g., FIG. 16). In accordance with a further aspect of the disclosure, a non-occluding medical balloon provides drug delivery by controlled surface emission of a drug or drug-carrying medium. In some embodiments, a non-occluding balloon delivers one or more drugs entirely by controlled surface emission. In other embodiments, the non-occluding balloon delivers one or more drugs by using both drug-eluting coating and controlled surface emission.

Figure 17:
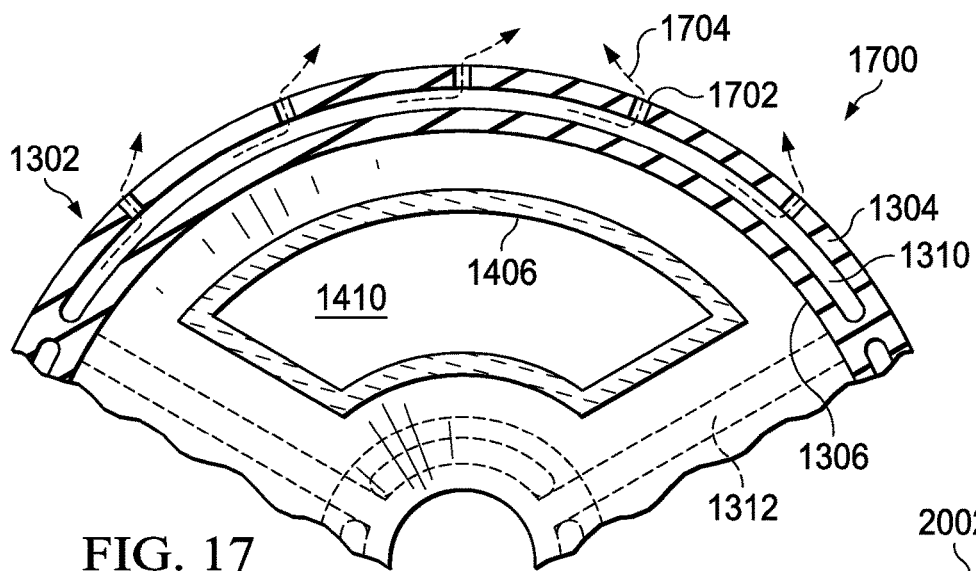
FIG. 17 is a cross-sectional view of a portion of an expanded balloon having micro-pores for drug delivery by controlled surface emission in accordance with additional aspects of the disclosure.

Referring now to FIG. 17, there is illustrated an exemplary medical balloon 1700 for drug delivery using controlled surface emission. The balloon 1700 is substantially similar in many respects to the balloons 1300 and 1500 previously described, therefore common reference numbers are used for similar elements. In FIG. 17, only a representative portion of the balloon 1700 is illustrated, the remaining structure having similar features. The sidewall 1302 of the balloon 1700 features a plurality of micro-pores 1702 extending through the outer surface (i.e., outer sidewall) 1304 of the sidewall 1302 into the inflation passage 1310. The micro-pores 1702 are holes through the outer surface 1304 of the sidewall that allow fluid to pass under controlled conditions from the inflation passage 1310 to the outer surface of the balloon. The dimensions of the micro-pores (denoted by subscript "MP") 1702, e.g., a length ($L_{MP}$) and a diameter ($D_{MP}$), are selected relative to the surface tension and/or viscosity of the fluid medium 1704 within the inflation passage 1310 such that the fluid medium is not released from the micro-pores until a predetermined pressure differential ($DP_{MP}$) is present between the inflation passage and the exterior of the balloon (e.g., inside the blood vessel). This predetermined release differential $DP_{MP}$ can be selected to allow pressurized inflation medium 1704 to fully inflate the balloon 1700 to a pressure below $DP_{MP}$ without significant emission of inflation medium from the micro-pores 1702. After inflation of the balloon 1700, the pressure of the inflation medium 1704 can be increased to a pressure above $DP_{MP}$, at which point the inflation medium will be emitted from the micro-pores 1702. The rate of release of the inflation medium 1704 from the micro-pores 1702 can be varied by varying the pressure of the inflation medium above $DP_{MP}$. Release of the inflation medium 1704 can be stopped by allowing the pressure of the inflation medium to fall below $DP_{MP}$. By including a drug in the inflation medium 1704, the release of the inflation medium 1704 through the micro-pores 1702 functions to deliver the drug directly to the surface of the balloon 1700.

The micro-pores 1702 can be formed in the outer sidewall 1304 using any known method for creating small precision holes in balloon materials. In some embodiments, mechanical or thermal method can be used to form the micro-pores 1702. However, for most embodiments, a laser drill or laser ablation apparatus can be used to bore the micro-pores 1702. For forming very small micro-pores 1702, an excimer or exciplex laser apparatus can be used.

Figure 18:
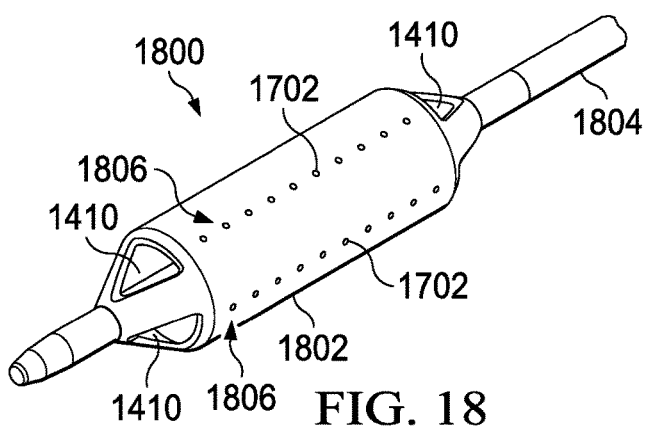
FIGS. 18 and 19 are perspective views of additional embodiments of non-occluding balloons having micro-pores.

Referring now to FIG. 18, there is illustrated one embodiment of an exemplary medical balloon apparatus 1800 for drug delivery using controlled surface emission. The apparatus 1800 includes a non-occluding balloon 1802 operatively connected to a catheter shaft 1804. The non-occluding balloon 1802 has perfusion ports 1410 disposed at each end and is similar to the non-occluding balloon 1700 previously described. The balloon 1802 includes a plurality of micro-pores 1702 arrayed in multiple longitudinal rows 1806 disposed on the central portion 1302' of the sidewall 1302. For purposes of illustration, the micro-pores 1702 in FIG. 18 are not shown to scale.

Figure 19:
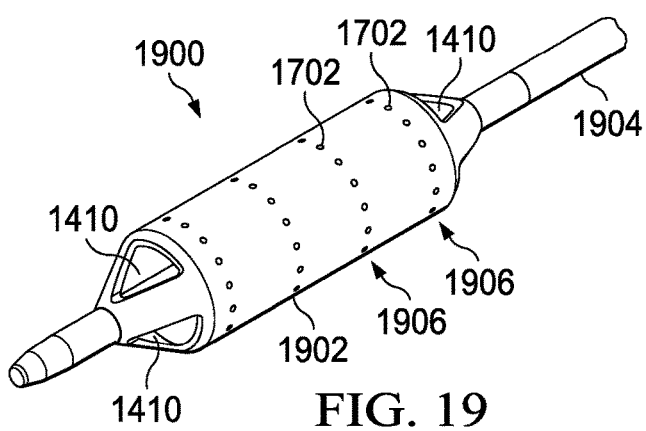

Referring now to FIG. 19, there is illustrated another embodiment of an exemplary medical balloon apparatus 1900 for drug delivery using controlled surface emission. The apparatus 1900 includes a non-occluding balloon 1902 operatively connected to a catheter shaft 1904. The non-occluding balloon 1902 has perfusion ports 1410 disposed at each end and is similar to the non-occluding balloon 1700 previously described. The balloon 1902 includes a plurality of micro-pores 1702 arrayed in ring 1906 disposed on the central portion 1302' of the sidewall 1302. For purposes of illustration, the micro-pores 1702 in FIG. 19 are not shown to scale. The number and arrangement of the micro-pores can be selected to correspond with desired drug application pattern and/or other drug-deliver requirements.

In other embodiments, a non-occluding balloon having multiple inflation passages 1310 can be provided, wherein at least some of the inflation passages are on a separate fluid circuits from the remaining inflation passages (i.e., they do not use a common fluid medium source). In such cases, the at least some inflation passages can be used for inflating the balloon, and the remaining (i.e., separate) inflation passages can be used for the delivery of drug-carrying fluid medium through micro-pores. In some such embodiments, only the remaining (i.e., separate) inflation passages can communicate with micro-pores, whereas in other embodiments, both the at least some inflation passages and the remaining inflation passage can communicate with separate sets of micro-pores, thereby allowing for the delivery of more than one drug by a single balloon.

Figure 20:
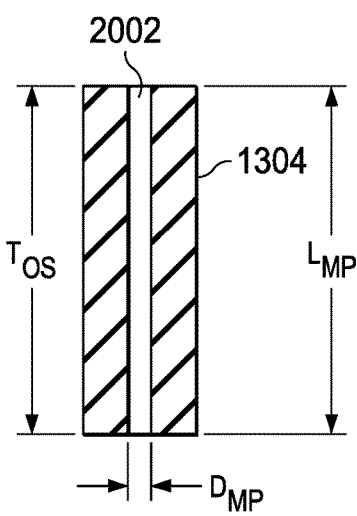
FIGS. 20 and 21 are cross-sectional side view of sections of outer sidewall containing micro-pores of different configurations.

Referring now to FIG. 20, there is illustrated a cross-section of a portion of an exemplary balloon outer sidewall 1304 having thickness $T_{OS}$ (i.e., the outer sidewall is denoted by subscript "OS") containing a single micro-pore 2002. In the illustrated embodiments, the micro-pore 1702 has a constant diameter $D_{MP}$ through the outer sidewall 1304, and thus has a length $L_{MP}=T_{OS}$. If the desired release pressure differential $DP_{MP}$ for the drug-carrying inflation medium can be achieved with micro-pore length $L_{MP}=T_{OS}$, then a constant diameter micro-pore can used. However, in some embodiments, a full-thickness micro-pore 1702 does not provide the desired $DP_{MP}$ for the selected drug-carrying inflation medium.

Figure 21:
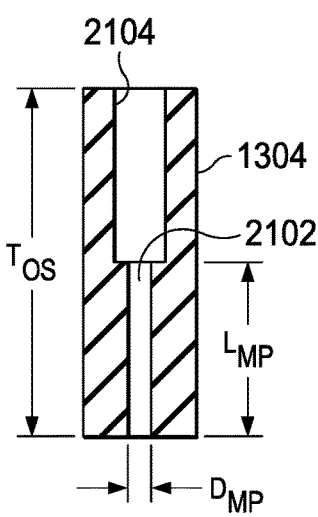

Referring now to FIG. 21, there is illustrated a cross-section of a portion of another exemplary balloon outer sidewall 1304 having thickness $T_{OS}$ containing a single micro-pore 2102. In this case, the hole through the outer sidewall 1304 does not have a constant diameter, but instead has a counter-bore 2104 of materially greater diameter than the micro-pore 2102 extending part of the thickness $T_{OS}$ such that the actual micro-pore with diameter $D_{MP}$ has a length $L_{MP}$ that is less than $T_{OS}$. The counter bore 2104 has a diameter that is materially greater than the micro-pore 2102, meaning that the surface tension/viscosity effects of the drug-carrying fluid medium are negligible in the counter-bore compared to the surface tension/viscosity effects in the micro-pore. The counter bore 2104 can be created by a first boring operation, and the micro-pore 2102 can be formed by a second boring operation. By using the counter-bore 2104 or other variable-geometry hole through the outer sidewall 1304, a wide range of release pressure differential pressures $DP_{MP}$ for the drug-carrying fluid medium can be achieved regardless of the nominal thickness of the outer sidewall material.

Figure 22:
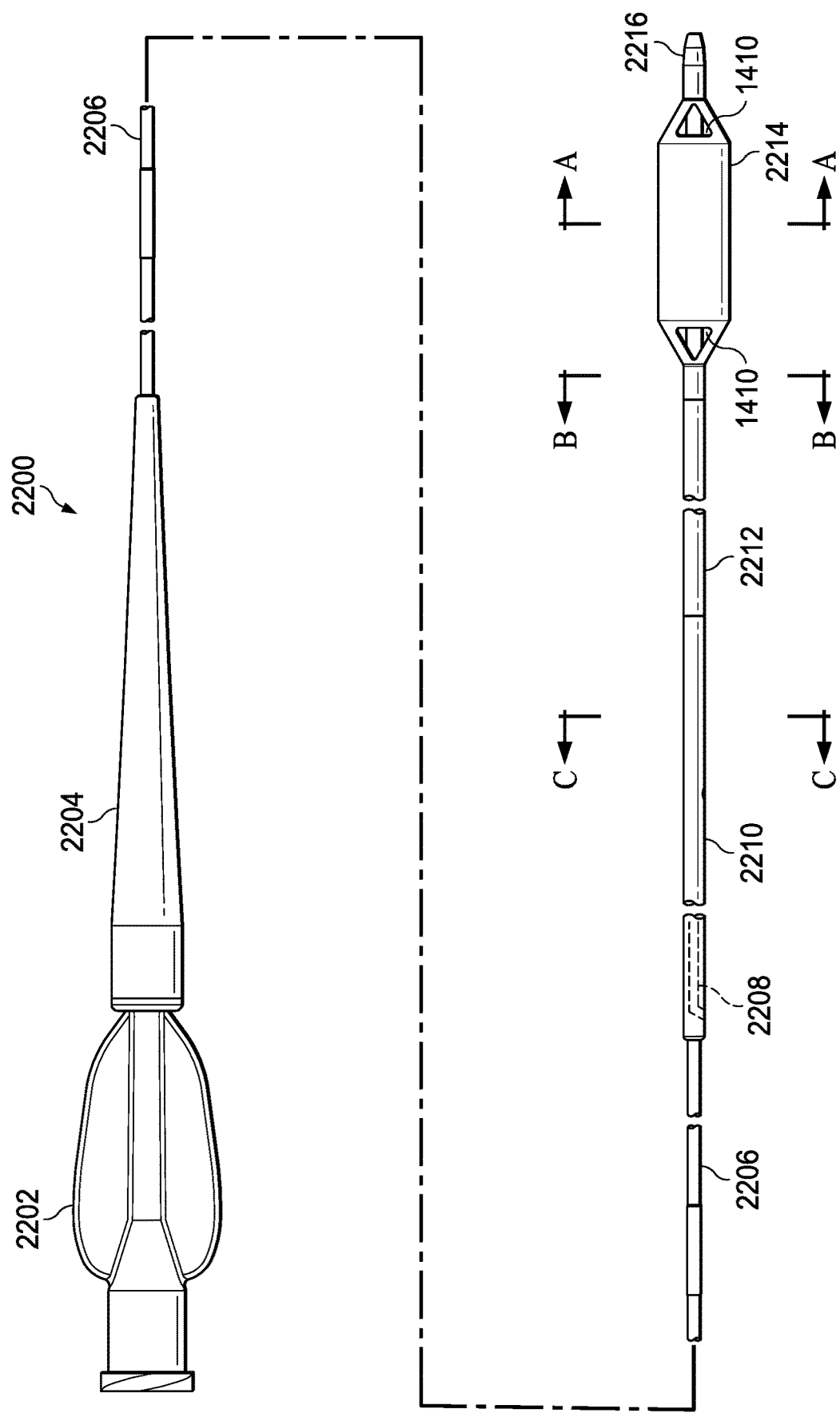
FIG. 22 is a side view of a complete catheter apparatus with non-occluding balloon for drug delivery in accordance with the disclosure.

Referring now to FIG. 22, there is illustrated a balloon catheter apparatus 2200 including a non-occluding balloon for drug delivery in accordance with the disclosure. The balloon catheter apparatus 2200 includes a catheter hub 2202, a strain relief 2204, a hypotube 2206, a guide wire lumen 2208, a section of relatively less flexible tubing 2210 (e.g., Pebax 72D) overlying a proximal portion of the guide wire lumen, a section of relatively more flexible tubing 2212 (e.g., Pebax 55D) overlying a distal portion of the guidewire lumen, a multi-lumen non-occluding balloon 2214 and a nosecone 2216. Unless otherwise described, the arrangement and construction of these components 2202, 2204, 2206, 2208, 2210, 2212 and 2216 are generally conventional for medical catheters. Further, the balloon catheter apparatus 2200 illustrated in FIG. 22 has a rapid-exchange ("RX") configuration; however other embodiments can have a concentric "over the wire" configuration, a multi-lumen configuration or other known configurations. FIG. 22 further includes exemplary length station information for the various components; however, these dimensions are not required and can vary in other embodiments. The non-occluding balloon 2214 of apparatus 2200 can have any of the previously disclosed configurations and can have a drug-eluting coating 124 applied to some or all of the outer surface 126 and/or include micro-pores 1702 for controlled emission of a drug-carrying fluid medium.

Figure 23:
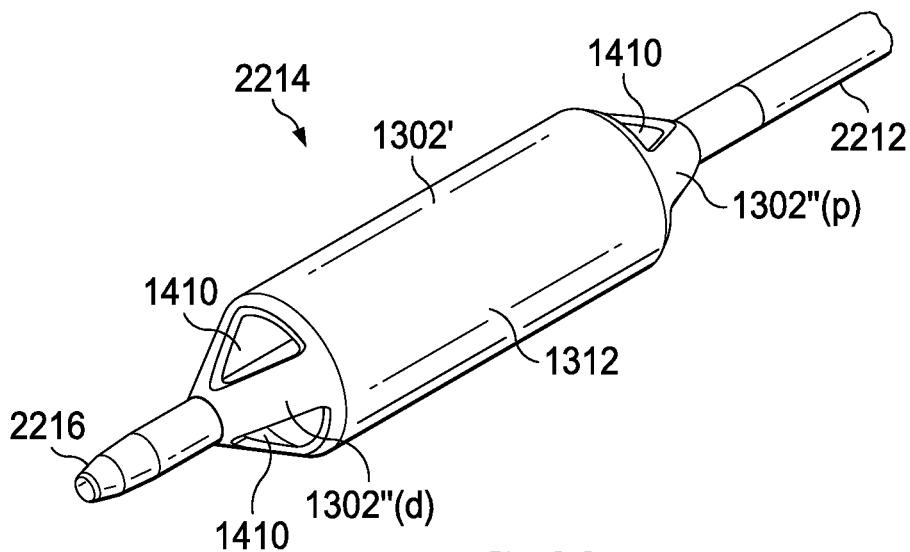
FIG. 23 is a perspective view of the balloon of FIG. 22.

Referring now to FIG. 23, an enlarged view of the non-occluding medical balloon 2214 is provided, illustrating the cylindrical central sidewall 1302' and the cone-shaped proximal end sidewall 1302"(p) and cone-shaped distal end sidewall 1302"(d). The balloon 2214 in FIG. 23 is semi-transparent, therefore certain internal components are visible. The balloon 2214 includes perfusion ports 1410 on each end sidewall 1302" and septums 1312 run between the inflation passages 1310 from the proximal end to the distal end of the balloon. The balloon 2213 can be used for drug delivery by using a drug coating 124 on the outer surface 1304 of the balloon and/or by direct emission of a drug-carrying medium from the inflation passages 1310 through micro-pores in the outer surface of the balloon.

Figure 24:
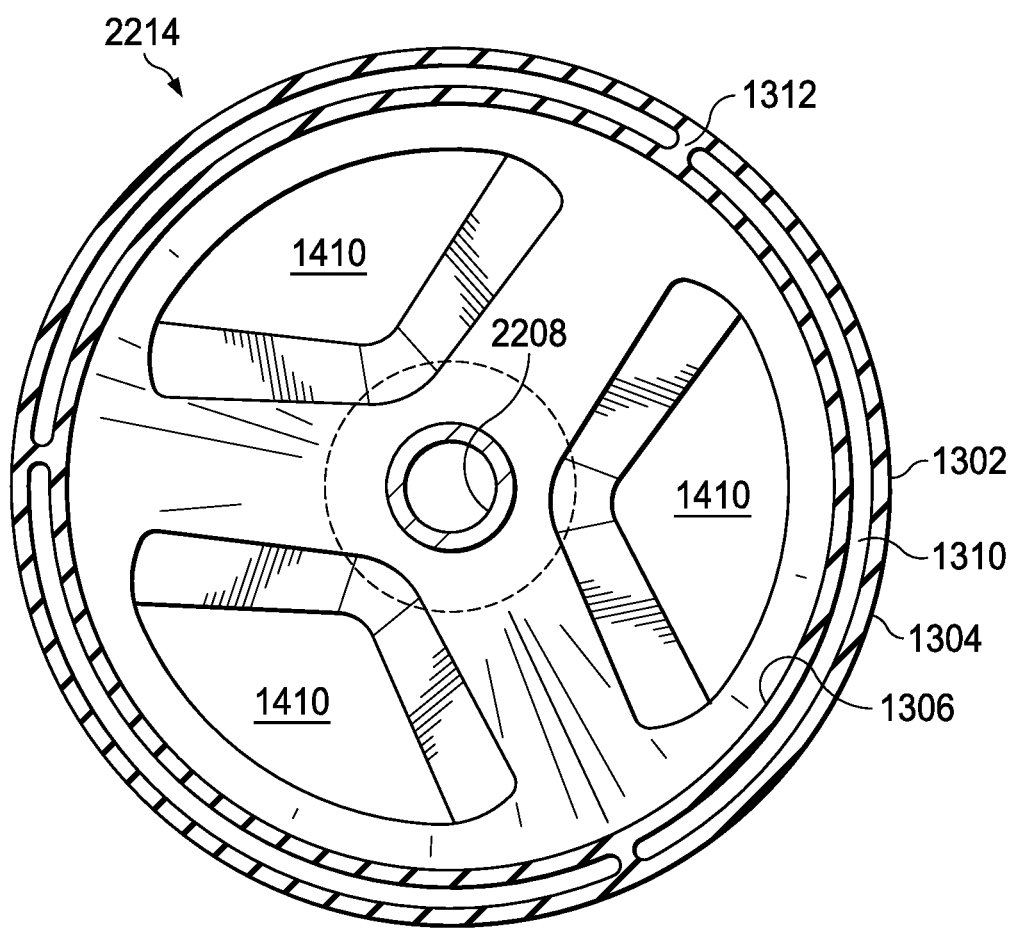
FIG. 24 is a cross-sectional end view taken along line A-A in FIG. 22.

Referring now to FIG. 24, there is illustrated a cross-sectional end view taken through section A-A in FIG. 22, showing the non-occluding medical balloon 2214 in the inflated configuration. The sidewall 1302, outer surface 1304, inflation passages 1310, septums 1312, perfusion ports 1410 and guidewire lumen 2208 are illustrated.

Referring now to FIGS. 25-29, additional details of the exemplary balloon catheter apparatus 2200 are illustrated. FIG. 25 is a cross-sectional view of the non-occluding balloon 2214 and adjacent catheter elements. The guide wire lumen 2208 runs through the central passage 1308 of the balloon. The sidewalls 1302 of the balloon 2214 are supported (when inflated) by pressurized inflation fluid in the inflation passages 1310 of the cone ends 1302" and the central portion 1302'.

Referring now to FIGS. 26-28, the connection of the exemplary catheter shaft to the balloon 2214 is illustrated. FIG. 27 is a cross-sectional end view taken through the catheter shaft along section C-C of FIG. 22 showing the guidewire lumen 2208 concentrically disposed within the Pebax sections 2210 and 2212, thereby forming an annular inflation lumen 2702 therebetween. The rapid exchange (RX) side-entry 2209 of the guidewire lumen 2208 can be seen in the background of FIG. 27. FIG. 28 is a cross-sectional end view taken through the unexpanded preform end 1200 along section B-B of FIG. 22. The guidewire lumen 2208 runs through the central passage 1208 of the unexpanded end 1200 with the inflation passages 1210 disposed in the sidewall 1202 between septums 1212. FIG. 26 is a cross-sectional side view of the junction between the catheter shaft and the unexpanded end 1200 of the balloon 2214. The junction includes an annular transition space 2602 which provides fluid communication between the annular inflation lumen 2702 of the catheter shaft and the multiple inflation passages 1210 of the balloon end 1200. As previously disclosed, the inflation passages 1210 are in fluid communication with the inflation passages 1310 of the balloon 2214.

Referring now to FIG. 29, there is illustrated a cross-sectional side view of the exemplary catheter shaft at a junction area 2902 between the hypotube 2206 and the rapid exchange portion having the concentrically-arranged guidewire lumen 2208 and the outer tubes 2210 and 2212. Within the junction area 2902, the inflation lumen 2904 at the center of the hypotube 2206 transitions to the annular inflation lumen 2702 between the inner guidewire lumen 2208 and outer tubes 2210 and 2212.

Figure 30:
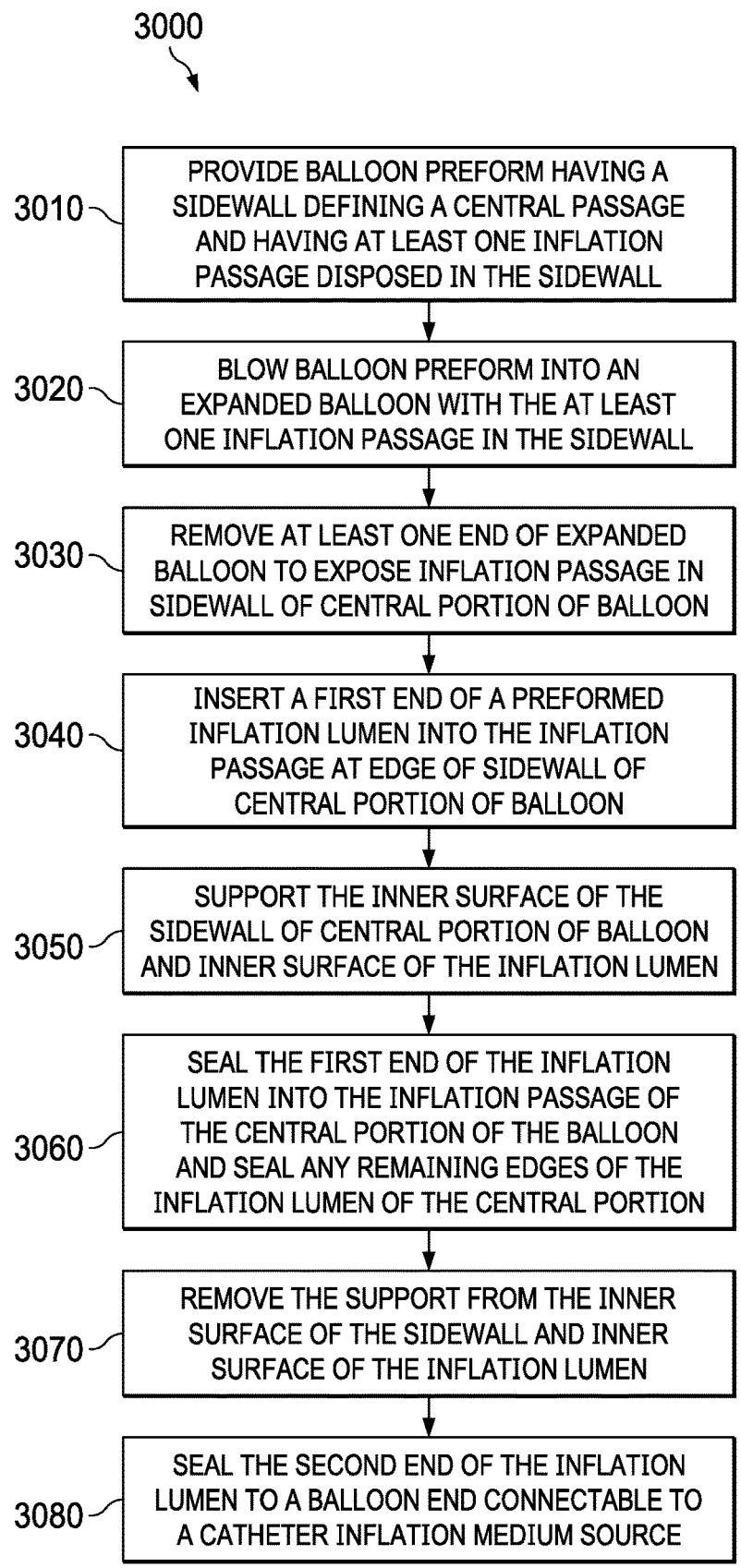
FIG. 30 is a schematic diagram of yet another method of fabricating a non-occluding medical balloon in accordance with a further embodiment.

Referring now to FIG. 30, there is illustrated a schematic diagram of yet another process 3000 for fabricating a non-occluding medical balloon in accordance with aspects of the invention. At step 3010, a balloon preform is provided having a sidewall defining a central passage and having at least one inflation passage disposed in the sidewall. At step 3020, the balloon preform is blown into an expanded balloon with the at least one inflation passage in the sidewall. As previously disclosed, blowing the balloon from a preform can include using a mold and pressurizing the central passage of the balloon preform to expand the sidewall against an inner surface of the mold to form the balloon. In some embodiments, the blown balloon includes an expanded center portion that can be of relatively constant diameter, tapered cone portions proximally and distally adjacent to the center portion, and respective proximal and/or distal tail portions (relatively unexpanded from the original preform) adjacent to the smaller end(s) of the cone portion(s). In some embodiments, the step 3020 can include heating the balloon preform and/or heating the mold. If heating is used, in many embodiments the temperature of the mold and/or preform will be limited to 50 degrees C. or less. At step 3030, at least one end of the expanded balloon is removed to expose (i.e., open) the inflation passage in sidewall of central portion of balloon. In some embodiments, the step 3030 includes cutting off an entire cone from the center portion of the sidewall, whereas in other embodiments, only a portion of the end cone is removed from the center portion. In some embodiments, the step 3030 can also comprise cutting off all or part of both end cones from the center portion of the sidewall. In addition to exposing/opening the inflation passage of the sidewall to the exterior of the balloon, the step 3030 also opens the center passage of the balloon to the exterior of the balloon.

Referring still to FIG. 30, at step 3040 of the process 3000, a first end of a preformed inflation lumen is inserted into the inflation passage at edge of sidewall of the central portion of balloon. At step 3050, the inner surface of the sidewall of the central portion of balloon is supported and the inner surface of the preformed inflation lumen is supported. In some embodiments, the step 3050 can comprise supporting the inner surface of the balloon sidewall by inserting a mandrel into the center passage of the balloon. In some embodiments, the step 3050 can comprise supporting the inner surface of the preformed inflation lumen by inserting a mandrel into the passage of the inflation lumen. In some embodiments, only the edge portion of the inner surface of the balloon sidewall is supported. At step 3060, the first end of the preformed lumen is sealed into the inflation passage of the central portion of the balloon and any remaining edges of the inflation passage (i.e., those remaining open to the exterior of the balloon) of the central portion are sealed. In some embodiments, the step 3060 can comprise melting or fusing the material of the preformed inflation lumen to the material of the balloon inflation passage and melting or fusing the remaining edges of the inflation passage to one another. At step 3070, the support is removed from the inner surface of the sidewall and the support is removed from the inner surface of the preformed inflation lumen. In some embodiments, the step 3070 can comprise removing mandrels from the preformed inflation lumen and/or center passage of the balloon. In step 3080, second end of the preformed inflation lumen is sealed to a balloon end connectable to a catheter inflation medium source. In some embodiments, the step 3080 can comprise connecting the second end of the preformed inflation lumen to an inflation lumen in a separate balloon end. In some embodiments, the step 3080 can comprise connecting the second end of the preformed inflation lumen to another inflation lumen that is annularly disposed around a guidewire lumen of the balloon.

Figure 31:
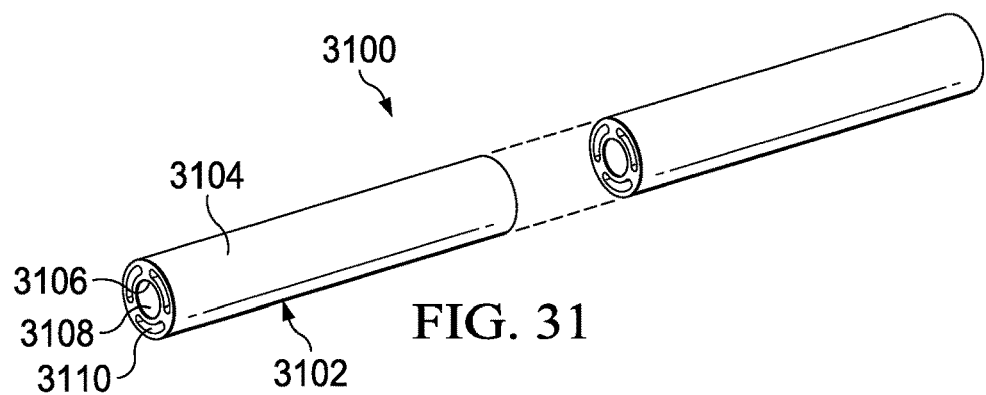
FIG. 31 shows a perspective view of an exemplary balloon preform in accordance with a still further aspect.

Referring now to FIGS. 31-37, there are illustrated further details of an exemplary non-occluding medical balloon according to the disclosure. Referring first to FIG. 31, there is illustrated a perspective view of a balloon preform 3100 having a sidewall 3102 with an outer surface 3104 and an inner surface 3106 defining a central passage 3108. Disposed in the sidewall 3102 between the inner surface 3106 and outer surface 3104 is at least one inflation passage 3110. In the illustrated embodiment, the preform 3100 includes three inflation passages 3110. In FIG. 31, a portion of the preform 3100 is shown broken away to illustrate that the central passage 3108 and inflation passages 3110 can extend continuously through the balloon preform.

Figure 32:
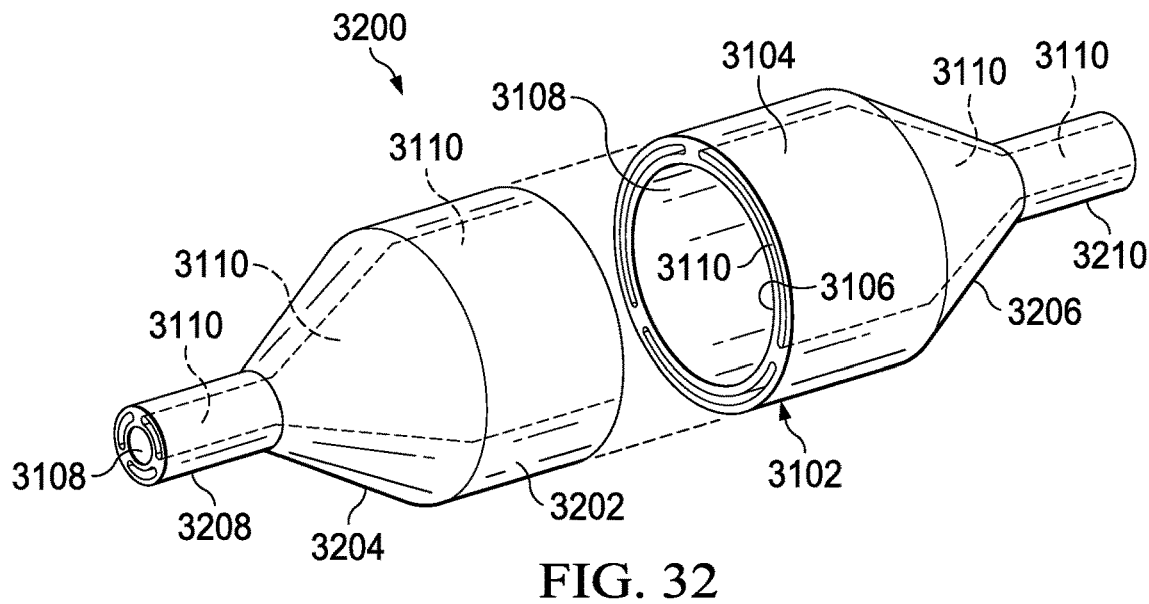
FIG. 32 shows an exemplary balloon body blown from the preform of FIG. 31.

Referring now to FIG. 32, the preform 3100 has been blown/expanded into a balloon body 3200 including a central portion 3202, respective proximal and distal cone portions 3204 and 3206, and respective proximal and distal tail portions 3208 and 3210. The proximal and distal tail portions 3208 and 3210 can be substantially unexpanded and thus have the same cross-sectional configuration as the preform 3100. In FIG. 32, a portion of the expanded central portion 3202 is shown broken away to illustrate that the central passage 3108 and inflation passages 3110 of the preform 3100 remain extending through the blown/expanded balloon. In other words, the sidewall 3102 of the balloon body 3200 can define the same central passage 3108 and have the same inflation passages 3110 as the preform 3100; however the dimensions (e.g., diameter) of the central passage, the dimensions (e.g., diameter and wall thickness) of the sidewall and the dimensions (e.g., width and height) of the inflation passages can be different from the corresponding structures in the preform due to the stretching of the balloon material that occurs during blowing.

Figure 33:
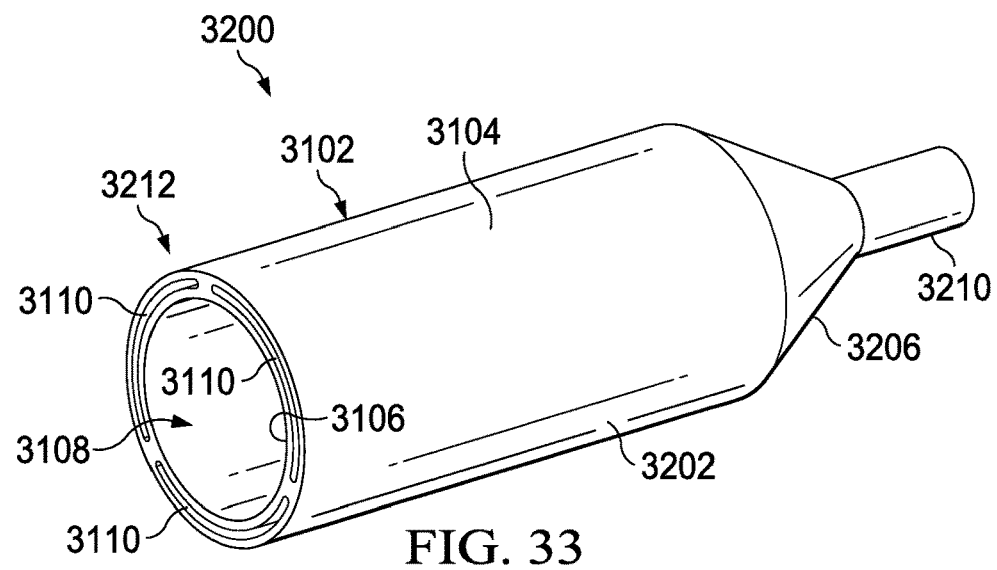
FIG. 33 shows the balloon body of FIG. 32 modified by removing an end cone.

Referring now to FIG. 33, at least one of the end cones has been removed from the balloon body 3200, thus exposing the edge 3212 of the sidewall 3102 and exposing (i.e., opening) the central passage 3108 and the inflation passages 3110 to the exterior of the balloon. In the illustrated embodiment, the entire proximal end cone 3204 (and also the proximal tail 3208) is removed. The removal of the cone can be performed by mechanical cutting, laser cutting or any known method for removing material from a medical balloon. In some embodiment, the distal cone 3206 can be removed instead of the proximal cone 3204, and in still other embodiments, both cones can be removed. In some embodiments, only a portion of the end cone or end cones can be removed from the center portion.

Figure 34:
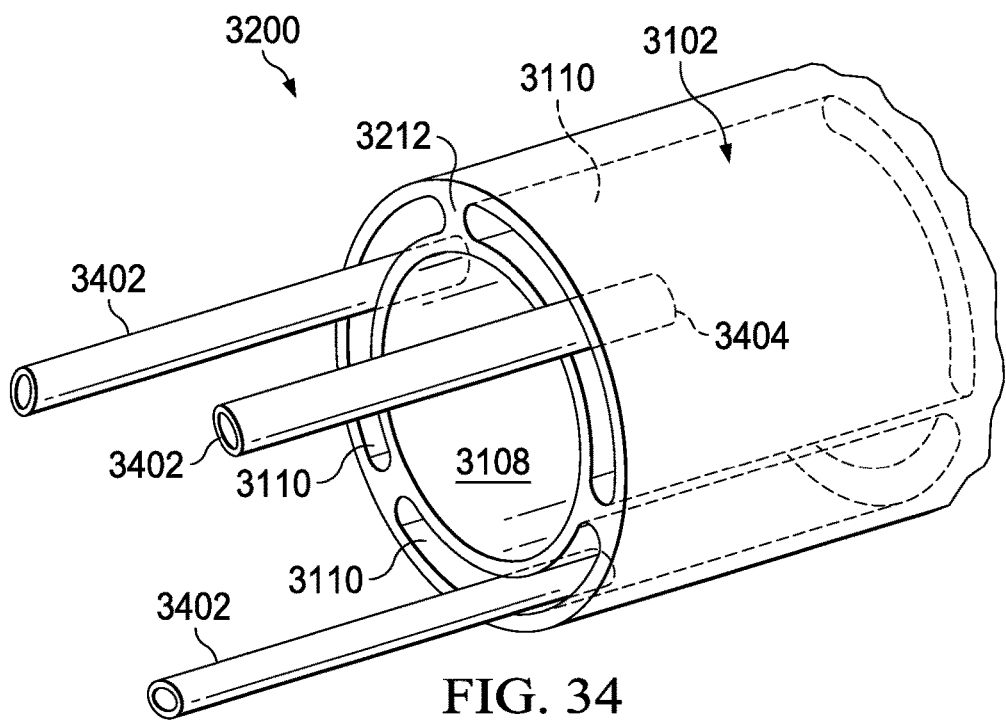
FIG. 34 is an enlarged view of an end portion of the balloon sidewall of FIG. 33, showing the insertion of preformed inflation lumens into the inflation passages of the sidewall.

Referring now to FIG. 34, a first end 3404 of a preformed inflation lumen 3402 is inserted into the inflation passage 3110 from the exposed edge 3212 of sidewall 3102 of the balloon body 3200. In the illustrated embodiment, the preformed lumens 3402 have an oval cross section; however in other embodiments, the preformed lumens can have various cross sections including circular, oval, rectangular or other shapes. In the illustrated embodiment, one preformed lumen 3402 is placed into each inflation passage 3110; however in other embodiments, different numbers of preformed lumens can be placed in each inflation passage and the same number of preformed lumens need not be placed in each inflation passage. The preformed inflation lumens 3402 can be made of the same material as the balloon sidewall 3102 or of a different material that can be fused or welded to the balloon sidewall.

Figure 35:
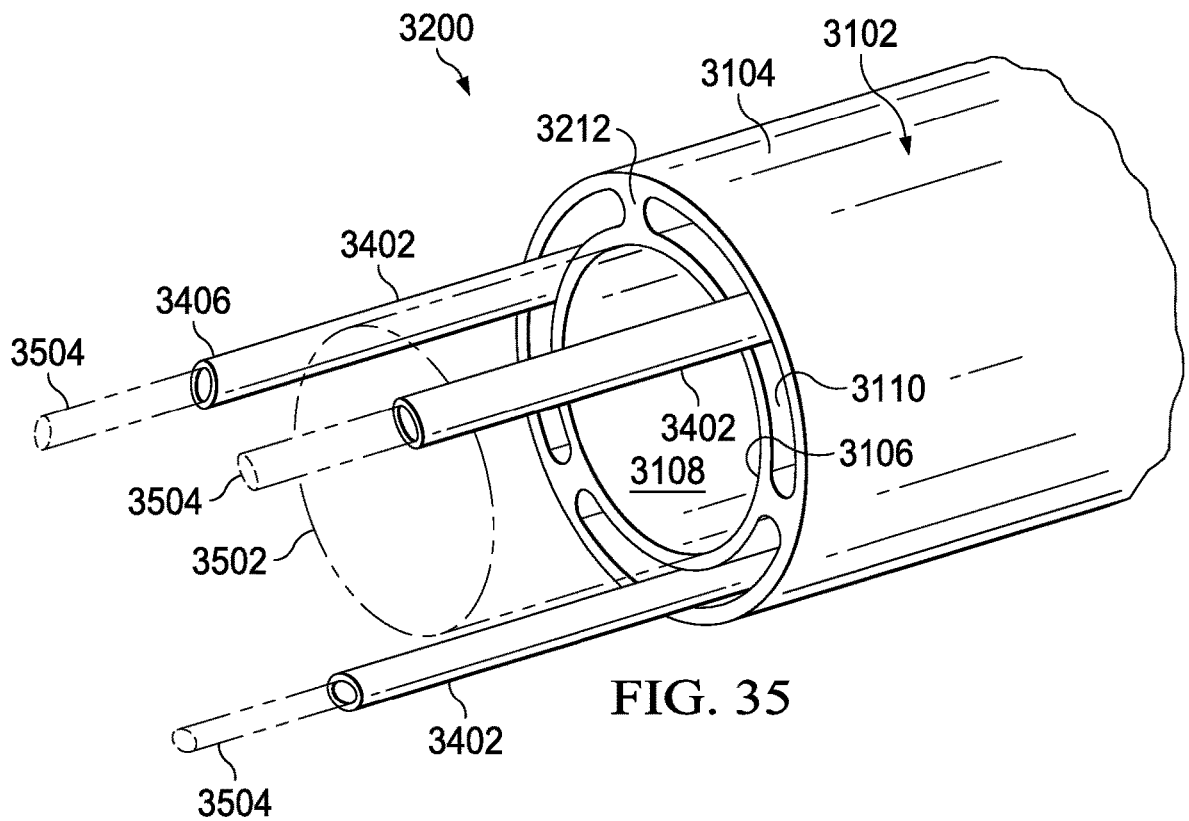
FIG. 35 shows supporting selective passages in the balloon body of FIG. 34.

Referring now to FIG. 35, the inner surface 3106 of the balloon body 3200 sidewall is supported and the inner surface of the preformed lumens 3402 are supported. In the illustrated embodiments, the inner surface 3106 of the sidewall 3102 is supported by a central mandrel 3502 (shown in dashed lines) removably inserted into the central passage 3108 and the inner surface of the preformed lumens 3402 are supported by lumen mandrels 3504 (shown in dashed lines) removably inserted into each respective passage of the preformed lumens, e.g., through second ends 3406. In other embodiments, support for the inner surface of the sidewall 3102 and/or the preformed lumens can be provided by other known support structures or support medium. In some embodiments, the inner surface 3106 of the balloon body 3200 sidewall and/or the inner surface of the preformed lumens 3402 are supported when the ends 3404 of the preformed lumens are placed in the inflation passages 3110, and in other embodiments the support is placed after the preformed lumens are inserted into the inflation passages.

While the inner surface 3106 of the balloon body 3200 sidewall is supported and the inner surface of the preformed inflation lumens 3402 are supported, the first end 3404 of each preformed lumen is sealed into the inflation passage 3110 of the sidewall 3102 of the balloon body 3200 and any remaining edges of the inflation passage (i.e., those edges 3212 remaining open to the exterior of the balloon) of the central portion are sealed. In some embodiments, the material of the preformed inflation lumen 3402 can be melted or fused to the material of the balloon sidewall 3102 surrounding the inflation passage 3110 and the remaining edges of the inflation passage can be melted or fused to one another.

Figure 36:
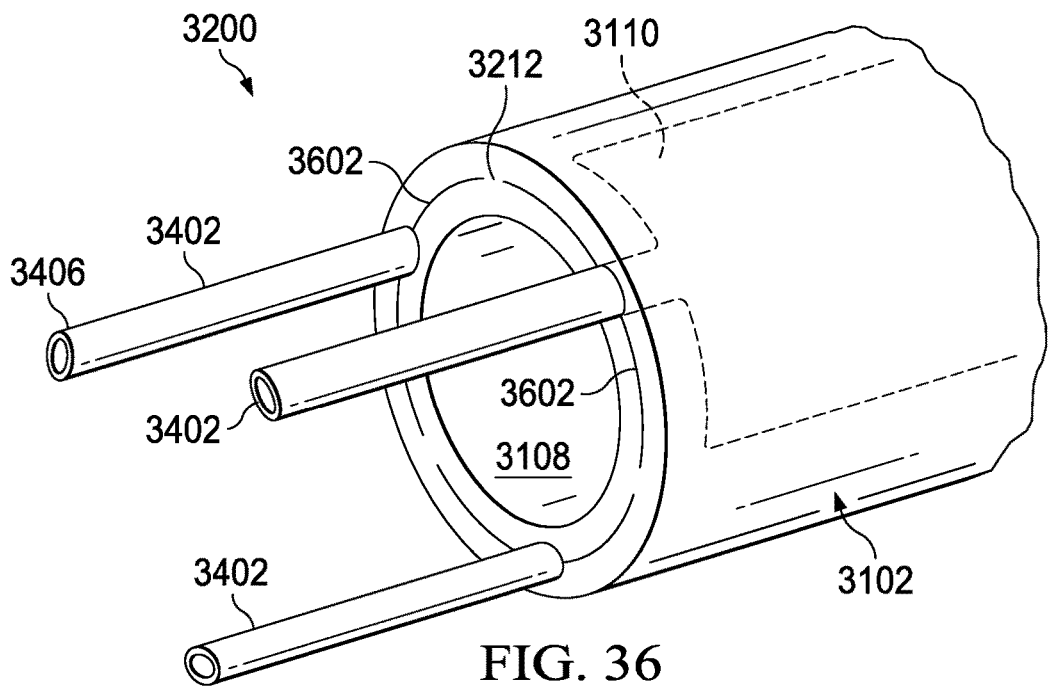
FIG. 36 shows the end portion of the balloon after the preformed inflation lumens are sealed in the inflation passages.

Referring now to FIG. 36, the edge 3212 of the central portion 3202 of the balloon body 3200 is illustrated after the preformed inflation lumens 3402 have been sealed in the inflation passages 3110 and the remaining edges of the inflation passages have been sealed to one another. In addition, the support (e.g., mandrels 3502 and 3504) has been removed for the inner surface of the sidewall 3102 and the inner surface of the preformed inflation lumens 3402. In the illustrated embodiment, a seam 3602 is visible where the sealing has occurred, however, other embodiments can have no visible seam. Each inflation passage 3110 in the sidewall 3102 of the balloon body 3200 can now be in fluid communication with a respective passage through the preformed inflation lumen 3402 to the respective second end 3406 of the lumen.

Figure 37:
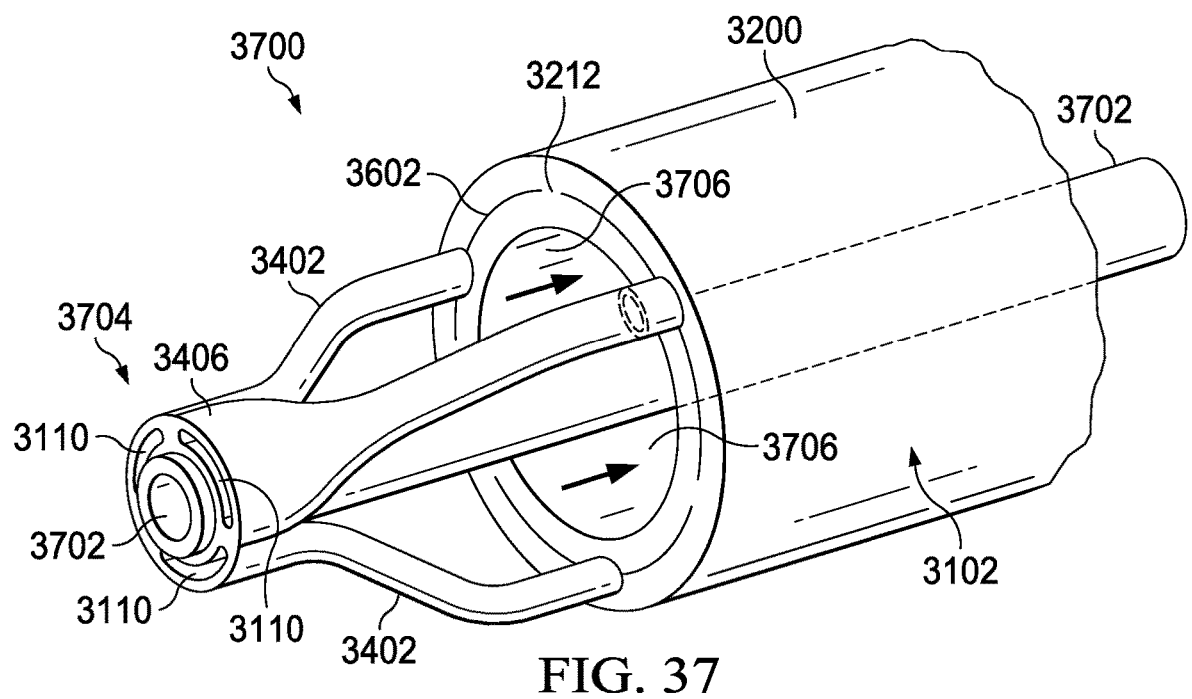
FIG. 37 shows the preformed inflation lumens of FIG. 36 formed into a balloon end around a guidewire lumen.

Referring now to FIG. 37, there is illustrated a non-occluding medical balloon 3700 formed from the balloon body 3200 with attached preformed inflation lumens 3402 and a guidewire lumen 3702. The guidewire lumen 3702 is disposed through the center passage 3108 of the balloon body 3200. The second ends 3406 of the preformed inflation lumens 3402 are formed into a balloon end 3704 attached to the guidewire lumen 3702. In the illustrated embodiment, the second ends 3406 of the three preformed inflation lumens 3402 are gathered together and formed into a balloon end 3704 having an annular configuration with the three inflation lumens (i.e., continuing from inflation passage 3110) changing shape (progressive cross-sections are shown in dashed lines) as the preformed inflation lumen transition from discrete tubes into a single annular ring. Perfusion ports or passages 3706 are formed between the preformed inflation lumens 3402 since the remainder of the central passage 3108 remains open at the end 3212.

In one embodiment, thermal molding can be used to form the preformed lumens 3402 into the balloon end 3704 using mandrels (not shown) within the preformed inflation lumens to position the lumens and maintain the desired interior shape of the inflation passages during thermal molding. In some embodiments, the balloon end 3704 can have separate inflation lumens 3110 and in other embodiments, the inflation lumens can be merged to a single annular inflation passage. In some embodiments, the balloon end 3704 can be formed around the guidewire lumen 3702, whereas in other embodiments, the balloon end can be formed separately, e.g., using a mandrel, and attached to the guidewire lumen in a separate operation.

The features disclosed in FIGS. 33-37 for forming perfusion ports 3706 at the proximal end of a balloon body 3200 can be used in substantially identical manner to form perfusion ports at the distal end of the balloon body. The balloon 3800 can be provided with any of the drug delivery features previously disclosed, including a drug eluting coating 124 on the outer surface 3104 of the balloon body and/or with micro-pores 2102 formed through the sidewall 3102 into the inflation passages 3110.

Figure 38:
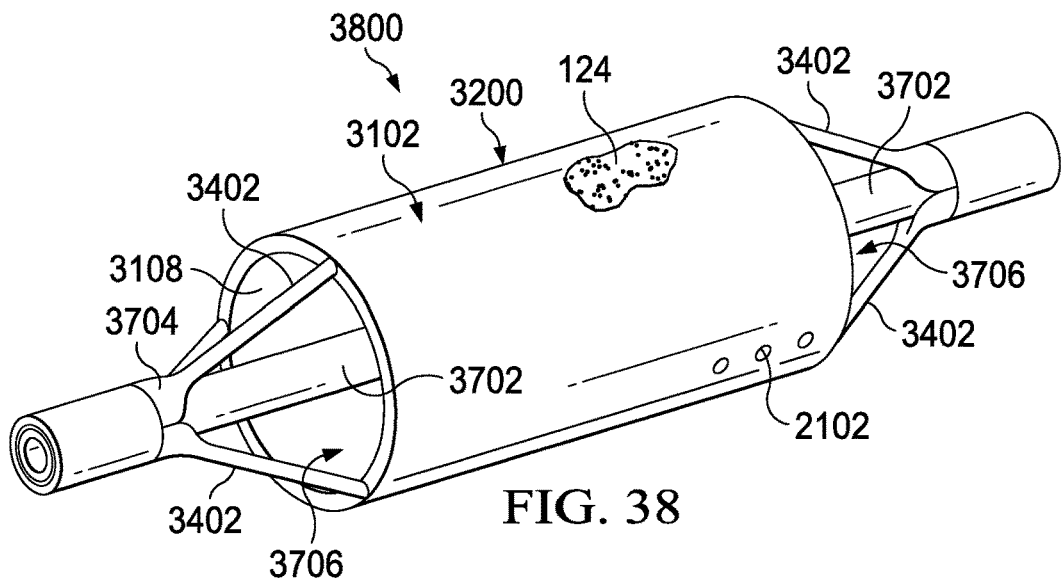
FIG. 38 shows non-occluding medical balloon for drug delivery having fabricated perfusion ports in accordance with another aspect of the disclosure.

Referring now to FIG. 38, there is illustrated a non-occluding medical balloon 3800 in accordance with another aspect of the disclosure having fabricated perfusion ports 3706 at both the proximal and distal ends of the balloon body 3200. The features disclosed in FIGS. 33-37 for forming perfusion ports 3706 at the proximal end of a balloon body 3200 can be used in substantially identical manner to form perfusion ports at the distal end of the balloon body. The balloon 3800 can be provided with any of the drug delivery features previously disclosed, including a drug eluting coating 124 on the outer surface 3104 of the balloon body and/or with micro-pores 2102 formed through the sidewall 3102 into the inflation passages 3110.

Figure 39:
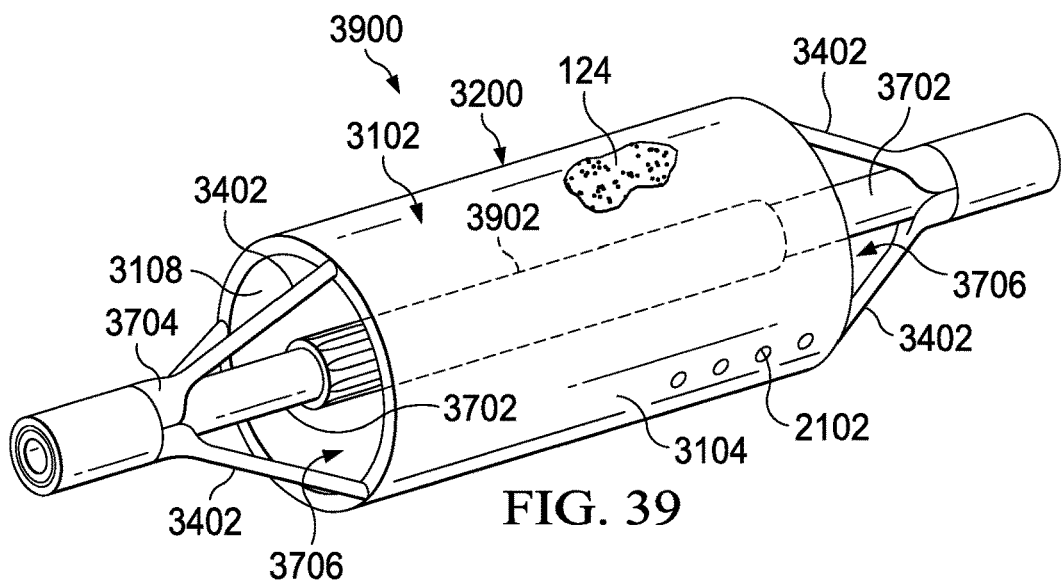
Figure 40:
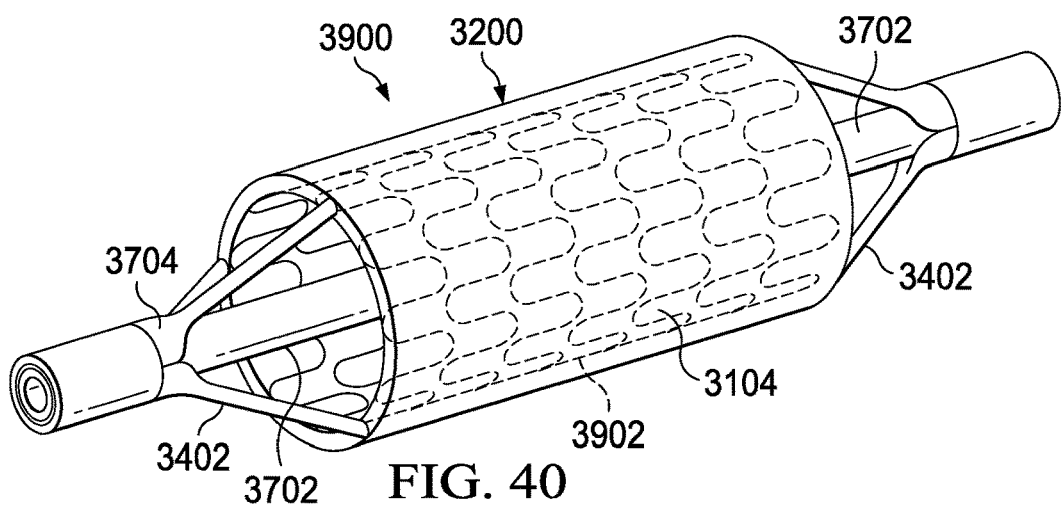

Referring now to FIGS. 39 and 40, there is illustrated a non-occluding medical balloon 3900 in accordance with yet another aspect of the disclosure. The balloon 3900 is substantially similar to balloon 3800, except a self-expanding structure 3902 is provided within the central passage 3108 of the balloon body 3200. The self-expanding structure 3902 can be a metallic or non-metallic stent or other structure that can selectively transition between a collapsed configuration (as illustrated in FIG. 39) and a larger, expanded configuration (illustrated in FIG. 40). In some embodiments, the self-expanding structure 3902 can be disposed inside the central passage 3108 of the balloon body 3200 prior to attachment of the preformed inflation lumens 3402 to the balloon sidewall 3102. The self-expanding structure 3902 can be deployed in accordance with known techniques for deploying stents or other support structures within the body. The self-expanding structure 3902 can provide additional support for the sidewall 3102 of the balloon 3900 to ensure that the outer surface 3104 contacts the surfaces of the body vessel when inflated.

The current disclosure provides non-occluding balloons, e.g., 1300 and, 1500, having perfusion ports 1410 formed through integral cones of the balloon body (i.e., "integral ports") and balloons, e.g., 3800 and 3900, having perfusion ports 3706 formed around preformed inflation lumens (i.e., "fabricated ports"). In one embodiment, a non-occluding medical balloon can have integral ports at both ends. In another embodiment, a non-occluding medical balloon can have integral ports at one end and fabricated ports at the other end. Some such embodiments can include a self-expanding structure disposed in the balloon body, and other such embodiments do not include a self-expanding structure. In yet another embodiment, a non-occluding medical balloon can have fabricated ports at ends. Some such embodiments can include a self-expanding structure disposed in the balloon body, and other such embodiments do not include a self-expanding structure. Any of the aforesaid embodiments can include a drug-eluting coating on the outer surface of the balloon body. Any of the aforesaid embodiments can include a plurality of micro-pores formed through the outer surface of the balloon body into the inflation passages.

Although the preferred embodiment has been described in detail, it should be understood that various changes, substitutions and alterations can be made therein without departing from the spirit and scope of the invention as defined by the appended claims.

What is claimed is:

1. A non-occluding medical balloon apparatus comprising:
 a proximal preform portion having a constant cross section along a central axis, the constant cross section defining a continuous annular preform sidewall having an outer surface, an inner surface defining a central passage, a plurality of preform inflation passages disposed between the outer and inner surfaces and fluidly isolated from the central passage, and a plurality of preform septums, each of the respective preform septums extending between the inner and outer surfaces of the continuous annular preform sidewall between a respective pair of the preform inflation passages to fluidly isolate the respective pair of preform inflation passages from one another;
 a nosecone defining an extension of the central passage;
 an expanded balloon portion disposed between, and connected to, the proximal preform portion and the nosecone, the expanded balloon portion including:
  a substantially cylindrical central portion having a nominal diameter that is greater than a distal diameter of the proximal preform portion and greater than a proximal diameter of the nosecone;
  wherein the central portion includes a continuous annular central sidewall having an outer surface, an inner surface defining a central portion of an expanded central passage, a plurality of central inflation passages disposed between the outer and inner surfaces, and a plurality of central septums, each of the respective central septums extending between the inner and outer surfaces of the continuous annular central sidewall between a respective pair of the central inflation passages to fluidly isolate the respective pair of central inflation passages from one another;
  wherein there is a one-to-one correspondence between each one of the preform inflation passages and a respective one of the central inflation passages, and a one-to-one correspondence between each one of the preform septums and a respective one of the central septums; and
  a proximal end portion connected between the central portion and the proximal preform portion and tapering from the nominal diameter of the central portion to the distal diameter of the proximal preform portion;
  wherein the proximal end portion includes a continuous annular proximal end sidewall having an outer surface, an inner surface defining a proximal end portion of the expanded central passage, a plurality of proximal end inflation passages disposed between the outer and inner surfaces, and a plurality of proximal end septums, each of the respective proximal end septums extending between the inner and outer surfaces of the continuous annular proximal end sidewall between a respective pair of the proximal end inflation passages to fluidly isolate the respective pair of proximal end inflation passages from one another;

wherein there is a one-to-one correspondence between each one of the preform inflation passages and a respective one of the proximal end inflation passages, and a one-to-one correspondence between each one of the preform septums and a respective one of the proximal end septums; and a distal end portion connected between the central portion and the nosecone and tapering from the nominal diameter of the central portion to the proximal diameter of the nosecone;

wherein the distal end portion includes a continuous annular distal end sidewall having an outer surface, an inner surface defining a distal portion of the expanded central passage, a plurality of distal end inflation passages disposed between the outer and inner surfaces, and a plurality of distal end septums, each of the respective distal end septums extending between the inner and outer surfaces of the continuous annular distal end sidewall between a respective pair of the distal end inflation passages to fluidly isolate the respective pair of distal end inflation passages from one another;

wherein there is a one-to-one correspondence between each one of the preform inflation passages and a respective one of the distal end inflation passages, and a one-to-one correspondence between each one of the preform septums and a respective one of the distal end septums; and wherein each respective preform inflation passage of the proximal preform portion is in fluid communication with the respective proximal end inflation passage, the respective central inflation passage and the respective distal end inflation passage having the respective one-to-one correspondence therewith of the expanded balloon portion;

wherein each respective preform septum of the proximal preform portion is operatively connected to respective proximal end septum, the respective central septum and the respective distal end septum having the respective one-to-one correspondence therewith of the expanded balloon portion, to collectively fluidly isolate the respective pair of preform inflation passages, the respective pair of proximal end inflation passages, the respective pair of central inflation passages and the respective pair of distal end inflation passages on each respective side thereof from one another;

wherein, on the proximal end portion of the expanded balloon portion, some overlying areas of the outer and inner surfaces of the continuous proximal end sidewall between a selected pair of proximal septums are joined to form a proximal sealed area;

wherein, a first hole is defined extending through the proximal sealed area of the continuous proximal end sidewall from an exterior of the balloon into the expanded central passage to form a proximal perfusion port, the first hole being fluidly isolated from the proximal end inflation passages;

wherein, on the distal end portion of the expanded balloon portion, some overlying areas of the outer and inner surfaces of the continuous distal end sidewall between a selected pair of distal septums are joined to form a distal sealed area;

wherein, a second hole is defined extending through the distal sealed area of the continuous distal end sidewall from the expanded central passage to the exterior of the balloon to form a distal perfusion port, the second hole being fluidly isolated from the distal end inflation passages; and a guide wire lumen is disposed through the central passage of the proximal preform portion, the respective expanded central passages of the balloon portion and the central passage of the nose cone.

2. The non-occluding medical balloon apparatus in accordance with claim 1, further comprising a drug-eluting coating disposed on the outer surface of the central portion of the balloon.

3. The non-occluding medical balloon apparatus in accordance with claim 2, wherein the drug-eluting coating comprises the drug Paclitaxel.

4. The non-occluding medical balloon apparatus in accordance with claim 1, further comprising a plurality of micropores formed through the outer surface of the sidewall into the inflation passage.

5. The non-occluding medical balloon apparatus in accordance with claim 4, wherein the dimensions of the micropores include a length $L_{MP}$ and a diameter $D_{MP}$, which are selected relative to a surface tension and/or to a viscosity of a fluid medium within the inflation passage such that the fluid medium is not released from the micro-pores until a predetermined pressure differential $D_{MP}$ is present between the inflation passage and the exterior of the balloon.

6. The non-occluding medical balloon apparatus in accordance with claim 1, further comprising:
    a catheter shaft attached to the proximal preform of the balloon, the catheter shaft including:
    a guide wire lumen; and
    an inflation lumen; and
    wherein the guide wire lumen of the catheter shaft is connected to the guidewire lumen of the balloon; and
    wherein the inflation lumen of the catheter shaft is fluidly connected to the inflation passages of the balloon.

7. The non-occluding medical balloon apparatus in accordance with claim 1, wherein the expanded central passage of the expanded balloon portion is empty except for the guide wire lumen.

* * * * *